(12) United States Patent
Neu et al.

(10) Patent No.: US 12,246,285 B2
(45) Date of Patent: Mar. 11, 2025

(54) METHODS AND SYSTEMS FOR SANITIZING AIR CONDITIONED BY A CLIMATE CONTROL SYSTEM

(71) Applicant: TRANE INTERNATIONAL INC., Davidson, NC (US)

(72) Inventors: Timothy J Neu, Cottage Grove, MN (US); Scott A. Waters, Lakeville, MN (US); Brad A. Wilke, Randolph, MN (US); Justin T. Srnec, Le Center, MN (US); Christos Alkiviadis Polyzois, Bloomington, MN (US)

(73) Assignee: TRANE INTERNATIONAL INC., Davidson, NC (US)

( * ) Notice: Subject to any disclaimer, the term of this patent is extended or adjusted under 35 U.S.C. 154(b) by 359 days.

(21) Appl. No.: 17/705,729

(22) Filed: Mar. 28, 2022

(65) Prior Publication Data
US 2022/0305881 A1    Sep. 29, 2022

Related U.S. Application Data

(60) Provisional application No. 63/166,702, filed on Mar. 26, 2021, provisional application No. 63/166,766, filed on Mar. 26, 2021.

(51) Int. Cl.
*B60H 1/00* (2006.01)
*A61L 9/04* (2006.01)
(Continued)

(52) U.S. Cl.
CPC ............. *B01D 53/346* (2013.01); *A61L 9/046* (2013.01); *B01D 53/44* (2013.01); *B01D 53/76* (2013.01);
(Continued)

(58) Field of Classification Search
CPC ............. B60H 3/0071; B60H 3/0078; B60H 1/00364; B60H 3/06; B01D 53/346
See application file for complete search history.

(56) References Cited

U.S. PATENT DOCUMENTS 8,128,869 B2    3/2012  Sunderland
2013/0232996 A1  9/2013  Goenka et al.
(Continued)

FOREIGN PATENT DOCUMENTS

CN    209341432    9/2019
CN    110425653    11/2019
(Continued)

OTHER PUBLICATIONS

JPH0314722 and translation (Year: 1991).*
(Continued)

*Primary Examiner* — Steven S Anderson, II
(74) *Attorney, Agent, or Firm* — HSML P.C.

(57) ABSTRACT

A method for purifying air within a space is provided. The method includes a controller determining whether an ON signal is received. Upon determining that the ON signal is received, the controller instructs an air sanitizer of an air sanitization system to turn ON to purify an airflow passing through the air sanitization system, and instructs an air movement fan/blower to operate in order to direct the airflow into the space. Upon determining that the ON signal is not received, the controller instructs the air movement fan/blower and the air sanitizer to be OFF.

18 Claims, 9 Drawing Sheets

(51) Int. Cl.
*B01D 53/34* (2006.01)
*B01D 53/44* (2006.01)
*B01D 53/76* (2006.01)
*B01D 53/86* (2006.01)
*B60H 3/06* (2006.01)
*F24F 8/24* (2021.01)

(52) U.S. Cl.
CPC ..... *B01D 53/8668* (2013.01); *B01D 53/8696* (2013.01); *B60H 1/00364* (2013.01); *B60H 1/00371* (2013.01); *B60H 1/00828* (2013.01); *B60H 3/06* (2013.01); *F24F 8/24* (2021.01); *A61L 2209/111* (2013.01); *B01D 2255/802* (2013.01); *B01D 2257/708* (2013.01); *B01D 2258/06* (2013.01); *B60H 2003/0675* (2013.01)

(56) References Cited

U.S. PATENT DOCUMENTS

2017/0051943 A1 2/2017 Hwang
2018/0280558 A1 10/2018 Mount
2022/0152265 A1* 5/2022 Eggers ............... A61L 9/20

FOREIGN PATENT DOCUMENTS

EP 3623714 3/2020
EP 3730852 10/2020
WO WO-2020088727 A1 * 5/2020

OTHER PUBLICATIONS

Extended European Search Report, issued in the corresponding European patent application No. 22164742.3, dated Aug. 5, 2022, 7 pages.

European Office Action, issued in the corresponding European patent application No. 22164742.3, dated Dec. 11, 2023, 5 pages.

* cited by examiner

METHODS AND SYSTEMS FOR SANITIZING AIR CONDITIONED BY A CLIMATE CONTROL SYSTEM

FIELD

This disclosure relates generally to a climate control system. More specifically, this disclosure relates to methods and systems for sanitizing air conditioned by a climate control system.

BACKGROUND

A transport climate control system can include, for example, a heating, ventilation and air conditioning (HVAC) system and/or a transport refrigeration system (TRS). An HVAC system is generally used to control a climate within a passenger space of a vehicle (e.g., a passenger bus, a cabin of a tractor, etc.). A TRS is generally used to control an environmental condition (e.g., temperature, humidity, air quality, and the like) within a cargo space of a transport unit (e.g., a truck, a container (such as a container on a flat car, an intermodal container, etc.), a box car, a semi-tractor, a bus, or other similar transport unit). The TRS can maintain environmental condition(s) of the cargo space to maintain cargo (e.g., produce, frozen foods, pharmaceuticals, etc.).

Society's vulnerabilities to a rapidly spreading virus were exposed during the COVID-19 pandemic. Transit vehicles typically service many riders in a day and have people regularly entering or leaving the vehicle. The passengers can be in close proximity, within an enclosed space in the transit vehicle. These conditions can facilitate the spread of communicable diseases and pathogens such as COVID-19. In particular, in a mobile society in which transportation is essential to commerce, e.g., the transport of good as well as the transport of people to jobs, schools, etc., legitimate hygienic solutions that foster confidence in various forms of transport are a benefit public health and safety.

SUMMARY

This disclosure is directed to methods and systems for sanitizing air conditioned by a climate control system.

The embodiments described herein can provide an effective air sanitization solution for use in climate control applications where there may be high air exchange rates. Accordingly, volatile organic compounds including, for example, viruses, pathogens, and bacteria can be effectively reduced in high air exchange rate climate control applications.

The embodiments described herein can also track an effectiveness of an air sanitization system used in a climate control application. Accordingly, a user can determine when a component of the air sanitization system (e.g., an air sanitizer) has lost sufficient efficacy and may need maintenance (e.g., repair or replacement).

It will be appreciated that the embodiments described herein can be applied to transport climate control applications as well as both residential HVAC applications and commercial HVAC applications.

In one embodiment, a method for purifying air within a climate controlled space is provided. The method includes a controller determining whether climate control is required for conditioning air within the climate controlled space. Upon determining that climate control is required, the controller: determining an amount of climate control required for conditioning air within the climate controlled space, instructing a compressor of a climate control system to operate to meet the amount of climate control required, instructing an air movement fan/blower of the climate control system to operate to meet the amount of climate control required, and instructing operation of an air sanitizer of an air sanitization system. Upon determining that climate control is not required, the controller: instructing an air movement fan/blower of the climate control system to operate at a predefined speed, and instructing operation of an air sanitizer of the air sanitization system.

In another embodiment, a system for purifying air within a climate controlled space is provided. The system includes an air sanitization system and a climate control system. The air sanitization system includes an air sanitizer configured to purify air passing through the air sanitization system. The climate control system includes a compressor configured to compress a working fluid, an evaporator coil configured to condition air passing over the evaporator coil, and an air movement fan/blower configured to direct conditioned air from the evaporator coil to the climate controlled space. The air sanitizer is positioned such that a majority of air passing over the evaporator coil is purified by the air sanitizer.

In yet another embodiment, a method for tracking effectiveness of an air sanitization system that includes an air sanitizer is provided. The method includes a controller monitoring operational parameter of the air sanitizer. The method also includes the controller determining that the air sanitizer is not operating effectively based on the operational parameter. Also, the method includes generating and displaying an alarm/maintenance notification to a user upon the controller determining that the air sanitizer is not operating effectively.

In another embodiment, a method for purifying air within a space is provided. The method includes a controller determining whether an ON signal is received. Upon determining that the ON signal is received, the controller instructs an air sanitizer of an air sanitization system to turn ON to purify an airflow passing through the air sanitization system, and instructs an air movement fan/blower to operate in order to direct the airflow into the space. Upon determining that the ON signal is not received, the controller instructs the air movement fan/blower and the air sanitizer to be OFF.

In another embodiment, a system for purifying air within a space is provided. The system includes an air sanitization system, and a controller. The air sanitization system includes an air sanitizer configured to purify an airflow passing through the air sanitization system. The system includes an air movement fan/blower configured to direct the airflow into the space. The controller is configured to determine whether an ON signal is received. Upon determining that the ON signal is received, the controller is configured to instruct the air sanitizer to turn ON to purify the airflow passing through the air sanitization system, and instruct the air movement fan/blower to operate in order to direct the airflow into the climate controlled space. Upon determining that the ON signal is not received, the controller is configured to instruct the air movement fan/blower and the air sanitizer to be OFF.

In another embodiment, a method for purifying air within a climate controlled space is provided. The method includes a controller determining whether an ON signal is received. Upon determining that the ON signal is received, the controller instructs an air sanitizer of an air sanitization system to turn ON to purify an airflow passing through the air sanitization system, and instructs an air movement fan/blower of a climate control system to operate in order to direct the airflow into the climate controlled space. Upon determining that the ON signal is not received, the controller instructs the air movement fan/blower and the air sanitizer to be OFF.

In another embodiment, a system for purifying air within a climate controlled space is provided. The system includes an air sanitization system, a climate control system, and a controller. The air sanitization system includes an air sanitizer configured to purify an airflow passing through the air sanitization system. The climate control system includes an air movement fan/blower configured to direct the airflow into the climate controlled space. The controller is configured to determine whether an ON signal is received. Upon determining that the ON signal is received, the controller is configured to instruct the air sanitizer to turn ON to purify the airflow passing through the air sanitization system, and instruct the air movement fan/blower to operate in order to direct the airflow into the climate controlled space. Upon determining that the ON signal is not received, the controller is configured to instruct the air movement fan/blower and the air sanitizer to be OFF.

BRIEF DESCRIPTION OF THE DRAWINGS

References are made to the accompanying drawings that form a part of this disclosure, and which illustrate embodiments in which the systems and methods described in this Specification can be practiced.

Like reference numbers represent like parts throughout.

DETAILED DESCRIPTION

This disclosure is directed to methods and systems for sanitizing air conditioned by a climate control system.

It will be appreciated that the embodiments described herein can be applied to transport climate control applications as well as both residential HVAC applications and commercial HVAC applications.

A transport climate control system is generally used to control one or more environmental conditions such as, but not limited to, temperature, humidity, air quality, or combinations thereof, of a transport unit. Examples of transport units include, but are not limited to a truck, a container (such as a container on a flat car, an intermodal container, a marine container, a rail container, etc.), a box car, a semi-tractor, a mass-transit vehicle (such as a passenger bus, a passenger train, etc.), or other similar transport unit. A climate controlled transport unit can be used to transport perishable items such as pharmaceuticals, produce, frozen foods, and meat products and/or can be used to provide climate comfort for passengers in a passenger space of a mass-transit vehicle. The transport climate control system may include a vapor-compressor type climate controlled system, a thermal accumulator type system, or any other suitable climate controlled system that can use a working fluid (e.g., refrigerant, etc.), cold plate technology, or the like.

A transport climate control system can include a climate control unit (CCU) attached to a transport unit to control one or more environmental conditions (e.g., temperature, humidity, air quality, etc.) of a climate controlled space of the climate controlled transport unit. The CCU can include, without limitation, a climate control circuit (including, for example, a compressor configured to compress a working fluid (e.g., refrigerant), a condenser, an expansion valve, and an evaporator), and one or more fans or blowers to control the heat exchange between the air within the climate controlled space and the ambient air outside of the climate controlled transport unit.

Figure 1A:
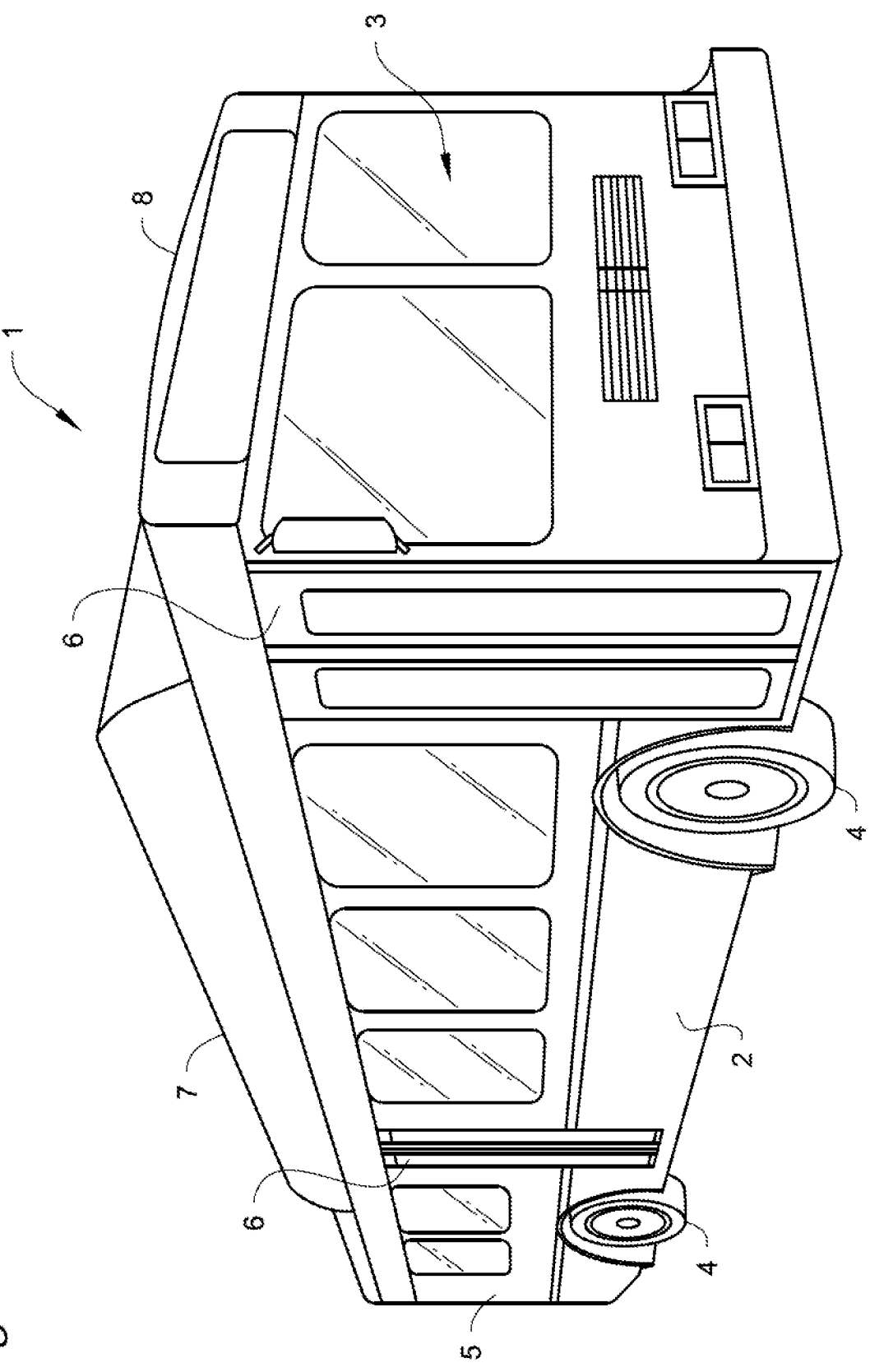
FIG. 1A illustrates a perspective view of a mass-transit vehicle including a transport climate control system, according to one embodiment.
Figure 1B:
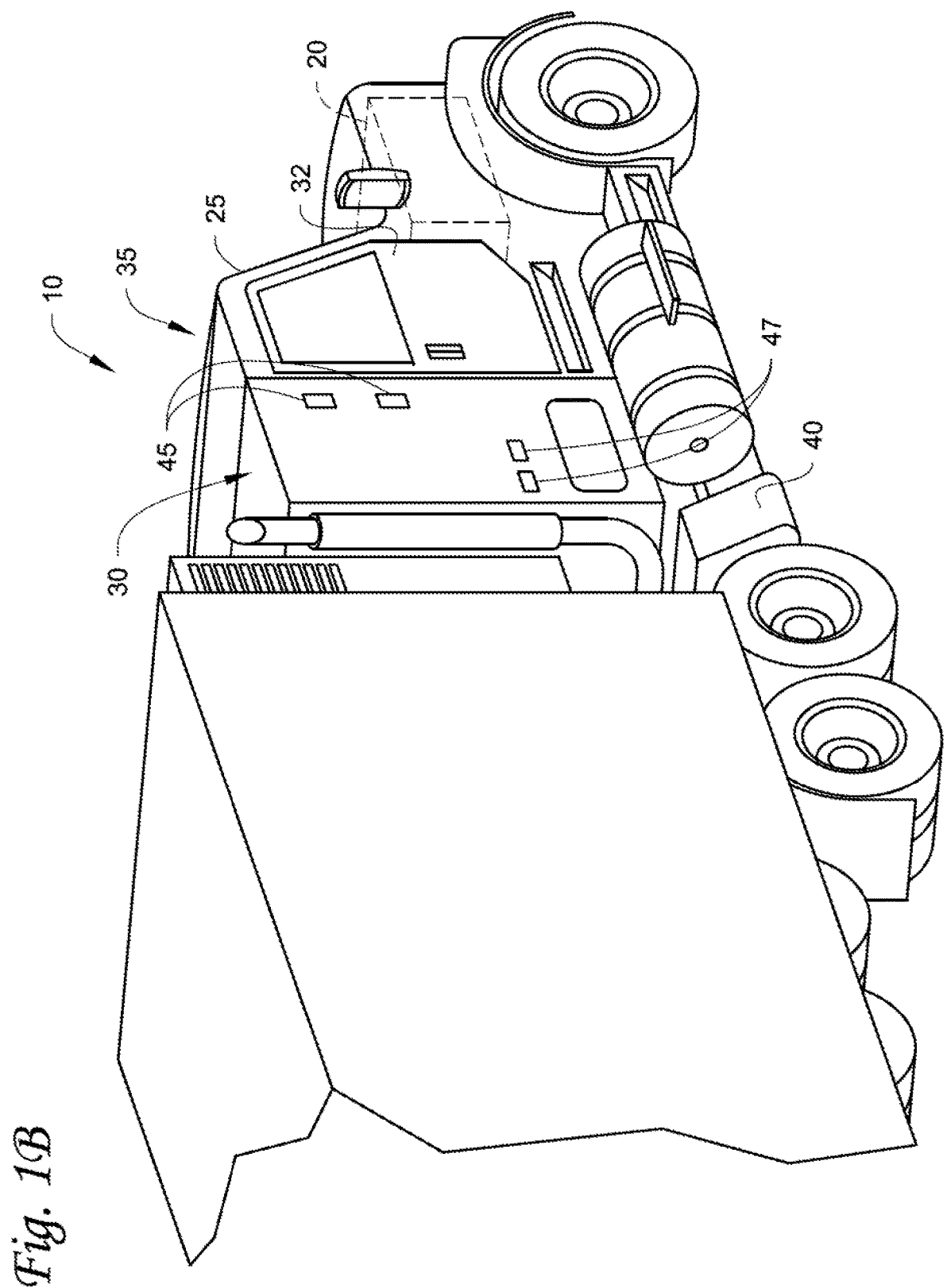
FIG. 1B illustrates a perspective view of a vehicle with an APU, according to an embodiment.
Figure 1C:
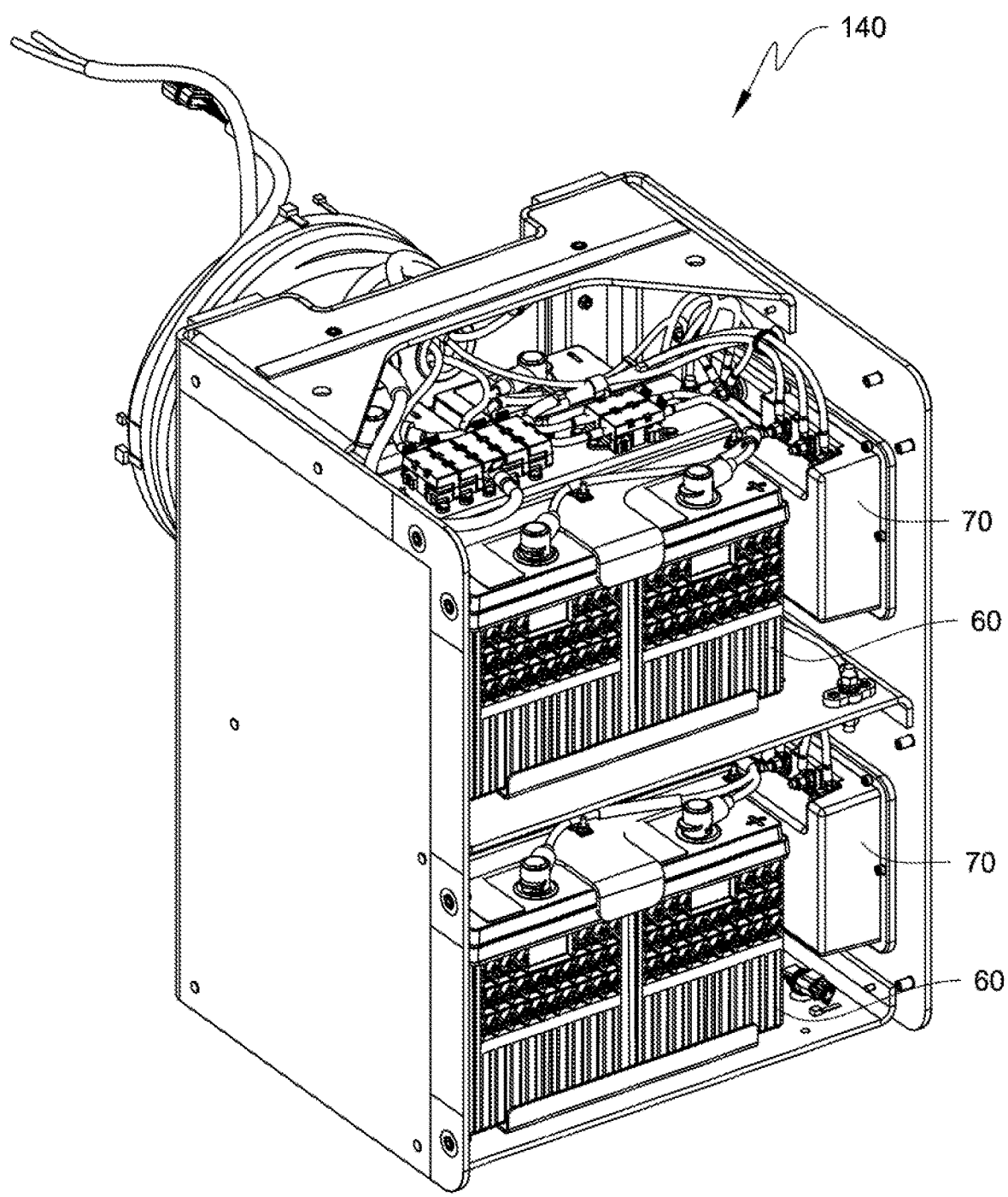
FIG. 1C illustrates a front perspective view of an APU, according to an embodiment.
Figure 1D:
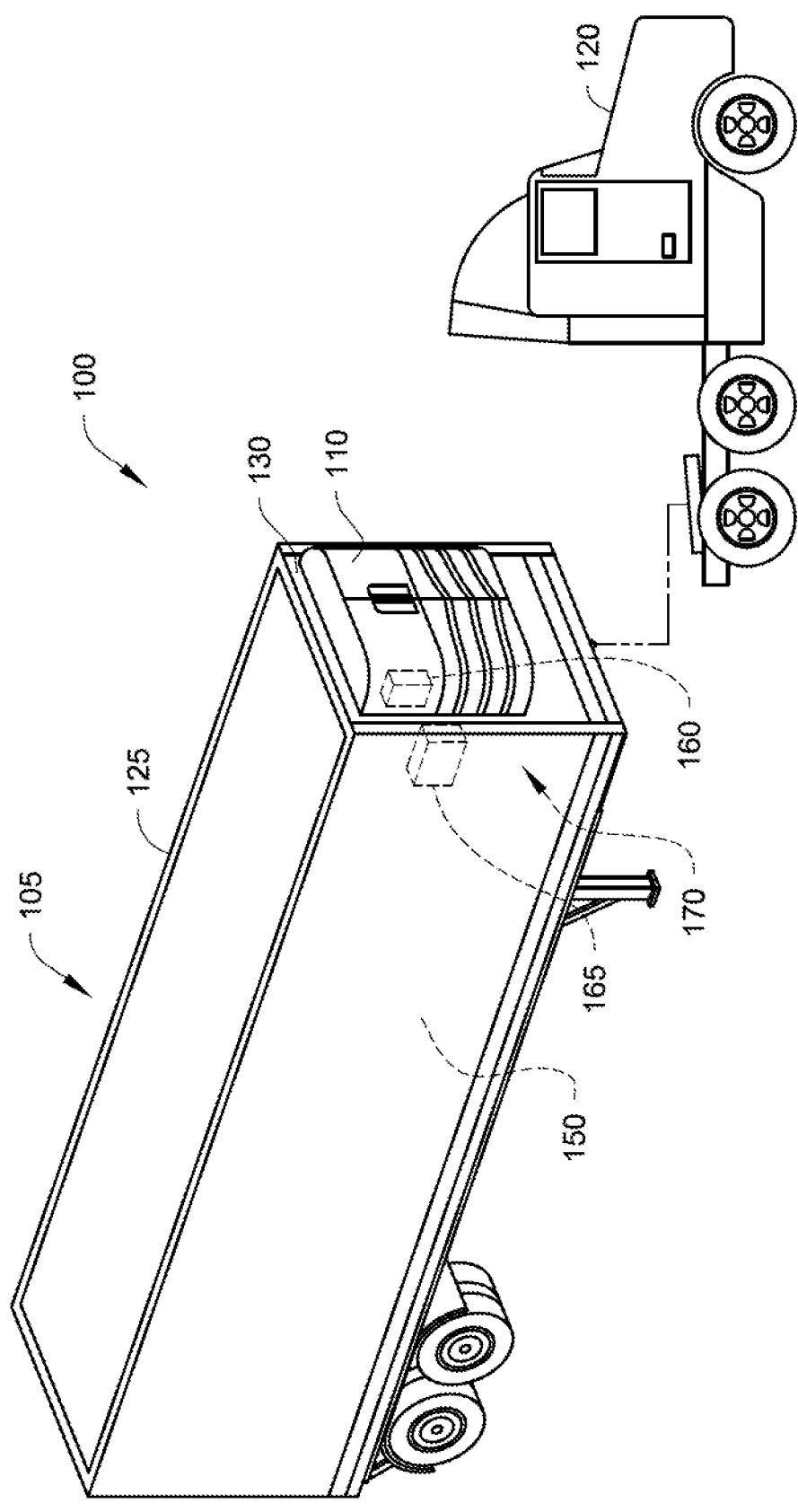
FIG. 1D illustrates a perspective view of a climate controlled transport unit attached to a tractor, according to one embodiment.

FIGS. 1A, 1B and 1D show various transport climate control systems. It will be appreciated that the embodiments described herein are not limited to the examples provided below, but can apply to any type of transport unit (e.g., a truck, a container (such as a container on a flat car, an intermodal container, a marine container, etc.), a box car, a semi-tractor, a passenger bus, or other similar transport unit), etc.

FIG. 1A is a perspective view of a mass-transit vehicle 1 including a climate control system, according to one embodiment. In the embodiment illustrated in FIG. 1A, the vehicle 1 is a mass-transit bus that can carry passenger(s) (not shown) to one or more destinations. In other embodiments, the vehicle 1 can be a school bus, railway vehicle, subway car, or other commercial vehicle that carries passengers. Hereinafter, the term "mass-transit vehicle" shall be used to represent all such vehicles, and should not be construed to limit the scope of the application solely to mass-transit buses.

FIG. 1A shows that the vehicle 1 includes a frame 2, a passenger compartment 3 supported by the frame 2, wheels 4, and a compartment 5. The frame 2 includes doors 6 that are positioned on a side of the vehicle 1. As shown in FIG. 1A, a first door 6 is located adjacent to a forward end of the vehicle 1, and a second door 6 is positioned on the frame 2 toward a rearward end of the vehicle 1. Each door 6 is movable between an open position and a closed position to selectively allow access to the passenger compartment 3.

The vehicle 1 also includes a climate control unit 7 attached to the frame 2 on a roof 8 of the vehicle 1. The climate control unit 7 is part of a transport climate control system (not shown) that is configured to provide climate control within the passenger compartment 3. In some embodiments, the climate control unit 7 can include a climate control circuit (not shown) with one or more fans/blowers to provide climate conditioned air within the passenger compartment 3. The climate control unit 7 can be combined with an air sanitization system (see FIG. 2) that is configured to purify air within the passenger compartment 3. While the climate control unit 7 is shown as a rooftop mount onto the roof 8, it will be appreciated that in other embodiments the climate control unit 7 can be located at other sides of the vehicle 1 (e.g., mounted to a rear end of the vehicle 1).

The compartment 5 is located adjacent the rear end of the vehicle 1, can include a power system (not shown) that is coupled to the frame 2 to drive the wheels 4. In some embodiments, the compartment 5 can be located in other locations on the vehicle 1 (e.g., adjacent the forward end, etc.).

FIG. 1B illustrates a vehicle 10 according to one embodiment. The vehicle 10 is a semi-tractor that is used to transport cargo stored in a cargo compartment (e.g., a container, a trailer, etc.) to one or more destinations. Hereinafter, the term "vehicle" shall be used to represent all such tractors and trucks, and shall not be construed to limit the invention's application solely to a tractor in a tractor-trailer combination. In some embodiments, the vehicle 10 can be, for example, a straight truck, van, etc.

The vehicle 10 includes a primary power source 20, a cabin 25 defining a sleeping portion 30 and a driving portion 35, an APU 40, and a plurality of vehicle accessory components 45 (e.g., electronic communication devices, cabin lights, a primary and/or secondary HVAC system, primary and/or secondary HVAC fan(s), sunshade(s) for a window/windshield of the vehicle 10, cabin accessories, etc.). The cabin 25 can be accessible via a driver side door (not shown) and a passenger side door 32. The cabin 25 can include a primary HVAC system (not shown) that can be configured to provide conditioned air within driving portion 35 and potentially the entire cabin 25, and a secondary HVAC system (not shown) for providing conditioned air within the sleeping portion 30 of the cabin 25. In some embodiments, the secondary HVAC system can be combined with an air sanitization system (see FIG. 2) that is configured to purify air within the sleeping portion 30 of the cabin 25. The cabin 25 can also include a plurality of cabin accessories (not shown). Examples of cabin accessories can include, for example, a refrigerator, a television, a video game console, a microwave, device charging station(s), a continuous positive airway pressure (CPAP) machine, a coffee maker, a secondary HVAC system for providing conditioned air to the sleeping portion 30.

The primary power source 20 can provide sufficient power to operate (e.g., drive) the vehicle 10 and any of the plurality of vehicle accessory components 45 and cabin accessory components 47. The primary power source 20 can also provide power to the primary HVAC system and the secondary HVAC system. In some embodiments, the primary power source can be a prime mover such as, for example, a combustion engine (e.g., a diesel engine, etc.).

The APU 40 is a secondary power unit for the vehicle 10 when the primary power source 20 is unavailable. When, for example, the primary power source 20 is unavailable, the APU 40 can be configured to provide power to one or more of the vehicle accessory components, the cabin accessories, the primary HVAC system and the secondary HVAC system. In some embodiments, the APU 40 can be an electric powered APU. In other embodiments, the APU 40 can be a prime mover powered APU. The APU 40 can be attached to the vehicle 10 using any attachment method. In some embodiments, the APU 40 can be turned on (i.e., activated) or off (i.e., deactivated) by an occupant (e.g., driver or passenger) of the vehicle 10. The APU 40 generally does not provide sufficient power for operating (e.g., driving) the vehicle 10. The APU 40 can be controlled by an APU controller 41.

FIG. 1C illustrates an electric APU 140 that can be used with a vehicle (e.g., the vehicle 10 shown in FIG. 1B), according to one embodiment. The APU 140 includes a plurality of energy storage elements 60 each of which is coupled to one of a plurality of converters 70. The converters 70 can provide electric power (e.g., AC or DC power) generated by the APU 140 to one or more vehicle accessory components, cabin accessory components, a primary HVAC system, and a secondary HVAC system. A secondary HVAC system can provide conditioned air to a sleeping portion of a vehicle cabin (e.g., the sleeping portion 30 of the cabin 25 shown in FIG. 1B). The energy storage elements 60 can be, for example, battery packs, fuel cells, etc. In some embodiments, the APU 140 can be turned on or off by an occupant (e.g., driver or passenger) of the vehicle. For example, the occupant can turn on the APU 140 to provide power stored in the energy storage elements 60 when a primary power source of the vehicle is turned off. It will be appreciated that the embodiments described herein can also be used with a prime mover powered APU.

In some embodiments, the APU (e.g., the APU 40 as shown in FIG. 1B and/or the APU 140 as shown in FIG. 1C) includes a vehicle electrical system.

FIG. 1D illustrates one embodiment of a climate controlled transport unit 105 attached to a tractor 110. The climate controlled transport unit 105 includes a climate control system 100 for a transport unit 125. The tractor 120 is attached to and is configured to tow the transport unit 125. The transport unit 125 shown in FIG. 1D is a trailer. It will be appreciated that the embodiments described herein are not limited to tractor and trailer units, but can apply to any type of transport unit (e.g., a container on a flat car, an intermodal container, etc.), a truck, a box car, or other similar transport unit. The transport unit 125 can include one or more doors (not shown) that are movable between an open position and a closed position to selectively allow access to a climate controlled space 150.

The climate control system 100 includes a climate control unit (CCU) 110 that provides environmental control (e.g. temperature, humidity, air quality, etc.) within the climate controlled space 150 of the transport unit 125. The climate control system 100 also includes a climate controller 170 and one or more sensors (not shown) that are configured to measure one or more parameters of the climate control system 100 and communicate parameter data to a climate controller 170.

The CCU 110 is disposed on a front wall 130 of the transport unit 125. In other embodiments, it will be appreciated that the CCU 110 can be disposed, for example, on a rooftop or another wall of the transport unit 125. The CCU 110 includes a climate control circuit (not shown) for conditioning air to be provided within the climate controlled space 150. The CCU 110 can also include a power system (see FIG. 2) to power components of the climate control system 100 (e.g., a compressor, one or more fans and blowers, one or more sensors, one or more solenoid valves, etc.). The CCU 110 can be combined with an air sanitization system (see FIG. 2) that is configured to purify air within the climate controlled space 150.

The programmable climate controller 170 may comprise a single integrated control unit 160 or that may comprise a distributed network of climate controller elements 160, 165. The number of distributed control elements in a given network can depend upon the particular application of the principles described herein. The climate controller 170 is configured to control operation of the climate control system 100.

Figure 2:
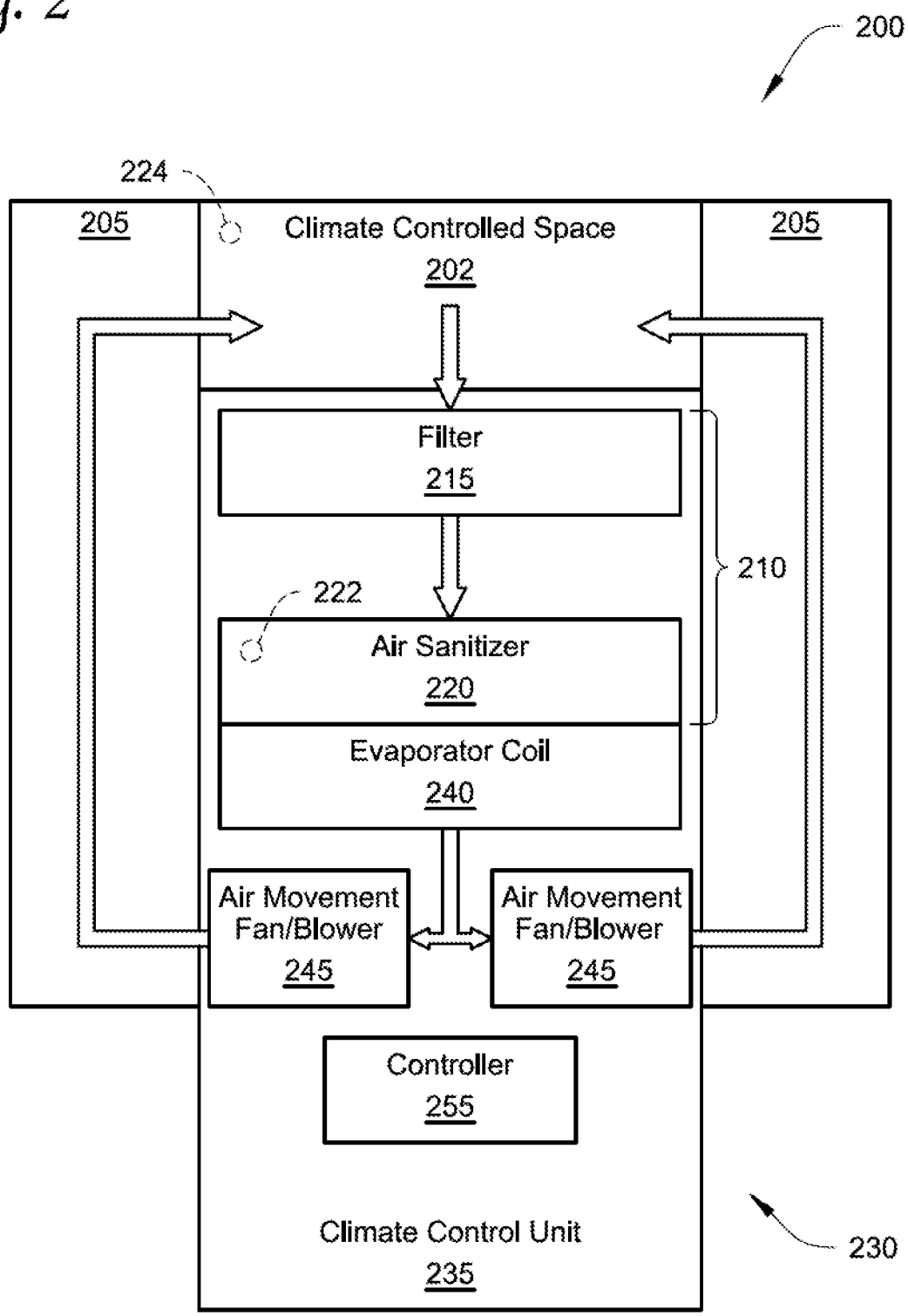
FIG. 2 illustrates block diagram schematic of a mass-transit vehicle that includes an air sanitization system and a transport climate control system, according to one embodiment.

FIG. 2 illustrates block diagram schematic of a mass-transit vehicle 200 that includes an air sanitization system 210 and a transport climate control system 230, according to one embodiment. The mass-transit vehicle 200 can be, for example, the mass-transit vehicle 1 shown in FIG. 1A. The mass-transit vehicle 200 includes a climate controlled space 202 for transporting one or more passengers travelling in the mass-transit vehicle 200. The mass-transit vehicle 200 can be, for example, a mass-transit bus (e.g., a school bus, a city bus, etc.), a railway vehicle, a subway car, or other mass-transit vehicle that carries passengers.

It will be appreciated that the embodiments described herein with respect to FIG. 2 are not limited to a mass-transit vehicle and can be used with other transport units including, for example, the vehicle 10 shown in FIG. 1B, the climate controlled transport unit 105 shown in FIG. 1D, etc. It will also be appreciated that the embodiments described herein with respect to FIG. 2 can also be applied in non-transport applications (e.g., residential HVAC applications, commercial HVAC applications, etc.)

The mass-transit vehicle 200 also includes two air delivery ducts 205. The climate controlled space 202 can be a passenger compartment for passengers travelling in the mass-transit vehicle 200. The climate controlled space 202 can optionally include one or more contamination sensors 224 that are configured to monitor air quality (e.g., contamination) within the climate controlled space 202. The one or more contamination sensors 224 can include one or more indoor air quality (IAQ) sensors and/or one or more contaminant sensors. In some embodiments, the one or more IAQ sensors can measure, for example, $CO_2$, total volatile organic compounds, particulate matter, temperature, humidity, etc. within the climate controlled space 202. In some embodiments, the one or more contaminant sensors can measure and identify specific species of contaminants in the air.

The air delivery ducts 205 are in airflow communication with both the climate controlled space 202 and a climate control unit 235 of the transport climate control system 230. The air delivery ducts 205 are configured to distribute climate controlled air generated by the climate control unit 235 into the climate controlled space 202. Each of the air delivery ducts 205 can include multiple openings (not shown) to distribute the climate controlled air substantially evenly within the climate controlled space 202. While the mass-transit vehicle 200 includes two air delivery ducts 205, it will be appreciated that the number of air delivery ducts 205 can vary as required by the mass-transit vehicle 200. For example, in another embodiment, the mass-transit vehicle 200 can include only a single air delivery duct 205. In some embodiments, the mass-transit vehicle 200 can also include one or more fresh air dampers (not shown) that can provide fresh air (e.g., ambient air outside of the mass-transit vehicle 200) downstream of an evaporator coil 240 of the climate control unit 235. It will be appreciated that the mass-transit vehicle 200 can also include one or more doors and/or windows (not shown) that can also introduce fresh air into the climate controlled space 202.

The air sanitization system 210 includes a filter 215 and an air sanitizer 220. The filter 215 can include a filter media that is configured to trap contaminants (e.g., dust particles, etc.) from an airflow passing through the filter 215. In some embodiments, the filter media can be a fabric filter media. In some embodiments, the filter 215 can have a multi-layer construction. In some embodiments, an anti-microbial coating can be applied to the filter 215. In some embodiments, the filter 215 can be a replaceable filter. It will be appreciated that the size of particles that can be trapped by the filter 215 can vary, for example, based on a minimum efficiency reporting values (MERV) rating. In some embodiments, the filter 215 can be a MERV 7 filter. In some embodiments, the filter 215 can be an electrostatic filter.

The air sanitizer 220 is configured to purify an airflow directed to the climate controlled space 202. In the embodiment shown in FIG. 2, the air sanitizer 220 is configured to purify the airflow that has first passed through the filter 215 and is passing through a climate control unit 235 of the transport climate control system 230. In particular, the air sanitizer 220 can attack volatile organic compounds (e.g., airborne viruses and bacteria) in the airflow passing there through. In some embodiments, the air sanitizer 220 can be a photo catalytic oxidation (PCO) air purifier that can emit hydroxyls, $H_2O_2$, ions, or the like that can attack any volatile organic compounds in the airflow passing there through. In particular, the PCO air purifier includes a light-activated catalyst configured to react with organic pollutants to oxidize them into a non-toxic substance.

In some embodiments, the PCO air purifier can be a graphene based PCO air purifier that uses a graphene enhanced titanium oxide catalyst to generate local hydroxyls that can attack volatile organic compounds when they come in contact with the air sanitizer 220. In some embodiments, the PCO air purifier can use an ultraviolet (UV) light to excite and activate the catalyst (e.g., a graphene enhanced titanium oxide catalyst) to begin the chemical reaction. The use of graphene can increase the amount of surface area that the titanium oxide is applied to and thus create more surface area for UV light to shine, thereby increasing the amount of hydroxyls generated. In some embodiments, the UV light can be generated using one or more light emitting diodes (LEDs), one or more mercury lamps, etc. In some embodiments, the UV light can generate ~390 nm light (e.g., when using one or more LEDs, the UV light generated can spike at around 395 nm). An advantage of using LEDs is that they can be safer than other types of light sources such as, for example, mercury light bulbs which can become dangerous should the mercury leak out of or otherwise be removed from the light bulb.

In some embodiments, the PCO air purifier of the air sanitizer 220 can include multiple LED panels. In some embodiments, each of the LED panels can include multiple LED circuits. For example, in one embodiment, each LED panel can include four LED circuits. In some embodiments, each of the multiple LED panels of the air sanitizer 220 can be independently controlled (e.g., turned ON or OFF) such that not all of the LED panels are ON at the same time. In some embodiments, the air sanitizer 220 can be a low voltage device that require, for example, ~24 VDC or less in order to operate.

In some embodiments, the air sanitizer 220 can include, for example, an ultraviolet germicidal irradiation (UVGI) air purifier, a bi-polar ionizer, a dry hydrogen peroxide generator, an ozone generator, etc.

It will be appreciated that in embodiments where the air sanitizer 220 emits, for example, hydroxyls, certain species of contaminants (e.g., halogens such as chlorine, fluorine, etc.) can become more toxic or dangerous when reacting with the hydroxyls (e.g., when oxidized). Accordingly, there can be embodiments whereby the air sanitizer 220 can be turned OFF when a level of certain species of contaminants are monitored by one or more contaminant sensors (of the one or more contamination sensors 224).

The air sanitization system 220 can optionally include one or more operational sensors 222 that can monitor operation of the air sanitizer 220 to ensure that the air sanitizer 220 is operating properly. In some embodiments, the one or more operational sensors 222 are configured to monitor one or more operational parameters of the air sanitizer 220. In some embodiments, the one or more operational sensors 222 can include one or more current sensors configured to monitor a current drawn by each of the multiple LED panels and/or each of the multiple LED circuits. In some embodiments, the one or more operational sensors 222 can include one or more power sensors configured to monitor a power drawn by each of the multiple LED panels and/or each of the multiple LED circuits. In some embodiments, the one or more operational sensors 222 can include one or more UV light sensors configured to monitor an intensity of the UV light. In some embodiments, the one or more operational sensors 222 can include one or more lumen sensors configured to monitor a luminance of each of the multiple LED panels and/or each of the multiple LED circuits. In some embodiments, the one or more operational sensors 222 can be replaced or used in conjunction with, for example, the one or more contamination sensors 224.

In some embodiments, transport climate control system 230 and the air sanitization system 210 are configured such that a majority if not an entire portion of the air flow passing over the evaporator coil 240 must also pass through the air sanitizer 220. In some embodiments, this can be achieved by mounting the air sanitizer 220 directly to the evaporator coil 240 such that the air sanitizer 220 covers the entire evaporator coil 240. In these embodiments, a majority if not the entire airflow can either pass through the air sanitizer 220 first before passing over the evaporator coil 240 or pass over the evaporator coil 240 first before passing through the air sanitizer 220. In some embodiments, the air sanitizer 220 can be located at other locations of the passenger vehicle 200 such as anywhere in the air delivery ducts 205. In these embodiments, the air sanitizer 220 can also be configured such that a majority if not the entire portion of the air flow directed to the climate controlled space 202 passes through the air sanitizer 220.

It will be appreciated that the mass-transit vehicle 200 can have high airflow rates within the climate controlled space 202. Applicant has found that hydroxyls, $H_2O_2$, ions, or the like that are emitted from typical PCO air purifiers may not survive long enough to travel from, for example, the evaporator coil 240, to the air movement fans/blowers 245, through the air delivery ducts 205 and into the climate controlled space 202 because of the length of travel and the high airflow rate. By providing an embodiment in which the air sanitizer 220 covers the entire evaporator coil 240, the air sanitization system 210 can require that all airflow passing over the evaporator coil 240 is first directed through the air sanitizer 220 to ensure that all conditioned air entering the climate controlled space is purified as it passes through the air sanitizer 220. Accordingly, any hydroxyls, $H_2O_2$, ions, or the like that are emitted by the air sanitizer 220 are not required or intended to travel to and enter the climate controlled space 202 in order to attack any volatile organic compounds in the air provided in the climate controlled space 202. This can prevent any harmful volatile organic compounds or ozone from being emitted by the air sanitization system 210 into the climate controlled space 202.

The transport climate control system 230 includes the climate control unit 235, a controller 255, and a plurality of climate control sensors (not shown). In some embodiments, the transport climate control system 230 can also include a human machine interface (HMI) configured to allow a user to manually communicate with and/or provide instructions to the transport climate control system 230, a telematics unit configured to wirelessly connect the transport climate control system 230 to user(s) and/or remote server(s) that are remote from the mass-transit vehicle 200. The climate control unit 235 includes an evaporator coil 240 and a plurality of air movement fans/blowers 245. The climate control unit 235 can also include a climate control circuit (not shown) that includes, for example, a compressor configured to compress a working fluid (e.g., a refrigerant), a condenser coil, the evaporator coil 240, and an expansion valve. The climate control circuit can include other components that are known in the art for conditioning air to be directed to a climate controlled space (e.g., one or more valves, a receiver tank, an economizer, working fluid lines, etc.). The climate control unit 235 can also include one or more condenser fans configured to direct air in a heat exchange relationship with the condenser coil out of the climate control unit 235 into the ambient outside of the mass-transit vehicle 200. The climate control sensors can be provided throughout the mass-transit vehicle 200 and monitor one or more climate control parameters. The climate control sensors, for example, can include: a return air temperature sensor that monitors the temperature of air returned from the climate controlled space 202 back to the climate control unit 235; a supply air temperature sensor that monitors the temperature of air supplied by the CCU 235 into the climate controlled space 122; a humidity sensor that monitors the humidity within the climate controlled space 202; an ambient temperature sensor that monitors the temperature outside of the mass-transit vehicle 200; a compressor suction pressure sensor that monitors a pressure at or near a suction port of the compressor; a compressor discharge pressure sensor that monitors a pressure at or near a discharge port of the compressor; etc.

The air movement fans/blowers 245 are configured to direct an airflow into the climate controlled space 205. The air movement fans/blowers 245 can be, for example, evaporator fans or blowers that are configured to direct conditioned air that has undergone a heat exchange while passing over the evaporator coil 240 into the air delivery ducts 205. It will be appreciated that the number of air movement fans/blowers 245 can vary based on the needs of the transport climate control system 230. For example, in some embodiments, the climate control unit 235 can include only a single air movement fans/blowers 245. In some embodiments, the air movement fans/blowers 245 can operate at multiple non-zero speeds (e.g., a low speed, a medium speed, and a high speed). In some embodiments, the low speed can be in a range of ~45-63% of a maximum speed of the air movement fans/blowers 245. In some embodiments, the medium speed can be in a range of ~55-75% of a maximum speed of the air movement fans/blowers 245. In some embodiments, the high speed can be in a range of ~65-88% of a maximum speed of the air movement fans/blowers 245. In some embodiments, the high speed can be about 100% of a maximum speed of the air movement fans/blowers 245. In some embodiments, the air movement fans/blowers 245 can be variable speed air movement fans/blowers that operate along a gradient range of non-zero speeds. In some embodiments, the air movement fans/blowers 245 can be low voltage devices that require, for example, ~24 VDC or less in order to operate. While FIG. 2 shows two air movement fans/blowers 245, it will be appreciated that in some embodiments the climate control unit 235 may include a single air movement fan/blower 245 or more than three air movement fans/blowers 245.

The controller 255 is configured to control operation of the transport climate control system 230 and can also control operation of the air sanitization system 210. In particular, the controller 255 is in electrical communication with the air movement fans/blowers 245, the compressor, the one or more condenser fans, the one or more valves, etc. Accordingly, the controller 255 can control operation of the transport climate control system by controlling operation of the air movement fans/blowers 245, the compressor, the one or more condenser fans, valves, etc. That is, the controller 255 can control whether the air movement fans/blowers 245, the compressor, the one or more condenser fans, one or more valves, etc. are ON or OFF. The controller 255 can also control a speed of the air movement fans/blowers 245, the compressor, the one or more condenser fans, etc. Also, the controller 255 can control the size of the opening of the one or more valves. The controller 255 is configured to receive climate control parameter data from the one or more climate control sensors. It will be appreciated that the controller 255 can use the climate control parameter data to control operation of the transport climate control system 230 and the air sanitization system 210.

In some embodiments, the controller 255 can also control operation of the air sanitizer 220. In particular, the controller 255 is in electrical communication with the air sanitizer 220. Accordingly, the controller 255 can turn the air sanitizer 220 ON or OFF as required and control the amount of power directed to the air sanitizer 220. In some embodiments, the controller 255 can selectively turn ON and OFF or limit the power provided to individual LED panels of the air sanitizer 220 while the air sanitizer 220 is in operation. For example, in some embodiments, the controller 255 can selectively turn OFF or limit power directed to a certain number of the LED panels while the air sanitizer 220 is in operation in order to reduce the purification capacity of the air sanitizer 220. The controller 255 can selectively turn OFF or reduce power to a certain number of the LED panels while the air sanitizer 220 is operating in order to reduce energy consumption of the air sanitizer 220 during, for example, periods when the mass-transit vehicle 200 may be lightly loaded, the risk of contamination in the climate controlled space is low, etc. Also, the controller 255 can rotate which of the multiple LED panels are ON and OFF or have reduced power to achieve uniform aging of the air sanitizer 220. In some embodiments, the controller 255 is configured to receive operational parameter data from the one or more operational sensors 222.

In some embodiments, the controller 255 can control the transport climate control system 230 and the air sanitization system 210 in a variety of operation modes. These operation modes, for example, can include: a continuous cooling mode whereby the compressor is continuously operating to provide cooling to the climate controlled space 202; a start-stop cooling mode whereby the compressor is periodically turned ON and OFF while providing cooling to the climate controlled space 202; a heating mode to provide heating to the climate controlled space 202; a defrost mode to defrost the evaporator coil 240; an air sanitization mode to purify air in the climate controlled space 202 by operating the air movement fans/blowers 245 at a high speed; etc.

In some embodiments, the controller 255 can be in communication with the mass-transit vehicle 200, a HMI of the transport climate control system 230, a telematics unit of the transport climate control system 230, etc. In some embodiments, the controller 255 can receive a communication signal from the mass-transit vehicle 200 when the mass-transit vehicle has been turned ON. For example, the controller can receive a signal from the mass-transit vehicle 200 that an ignition switch of the mass-transit vehicle 200 has been turned ON.

FIG. 2 shows arrows to illustrate how an airflow is directed through the mass-transit vehicle 200, according to one embodiment. In particular, air in the climate controlled space travels into climate control unit 235 and passes through the filter 215. The airflow passing through the filter 215 is then directed through the air sanitizer 220 to be purified and then over the evaporator coil 240 to be conditioned. The air movement fans/blowers 245 then directs the purified and conditioned airflow past the evaporator coil and into the air delivery ducts 205. The air delivery ducts 205 then return purified and conditioned air back into the climate controlled space 202. One embodiment of a method for operating the air sanitization system 210 and the transport climate control system 230 is described below with respect to FIG. 3. Also, one embodiment of a method for tracking effectiveness of the air sanitization system 210 is described below with respect to FIG. 4.

Figure 3:
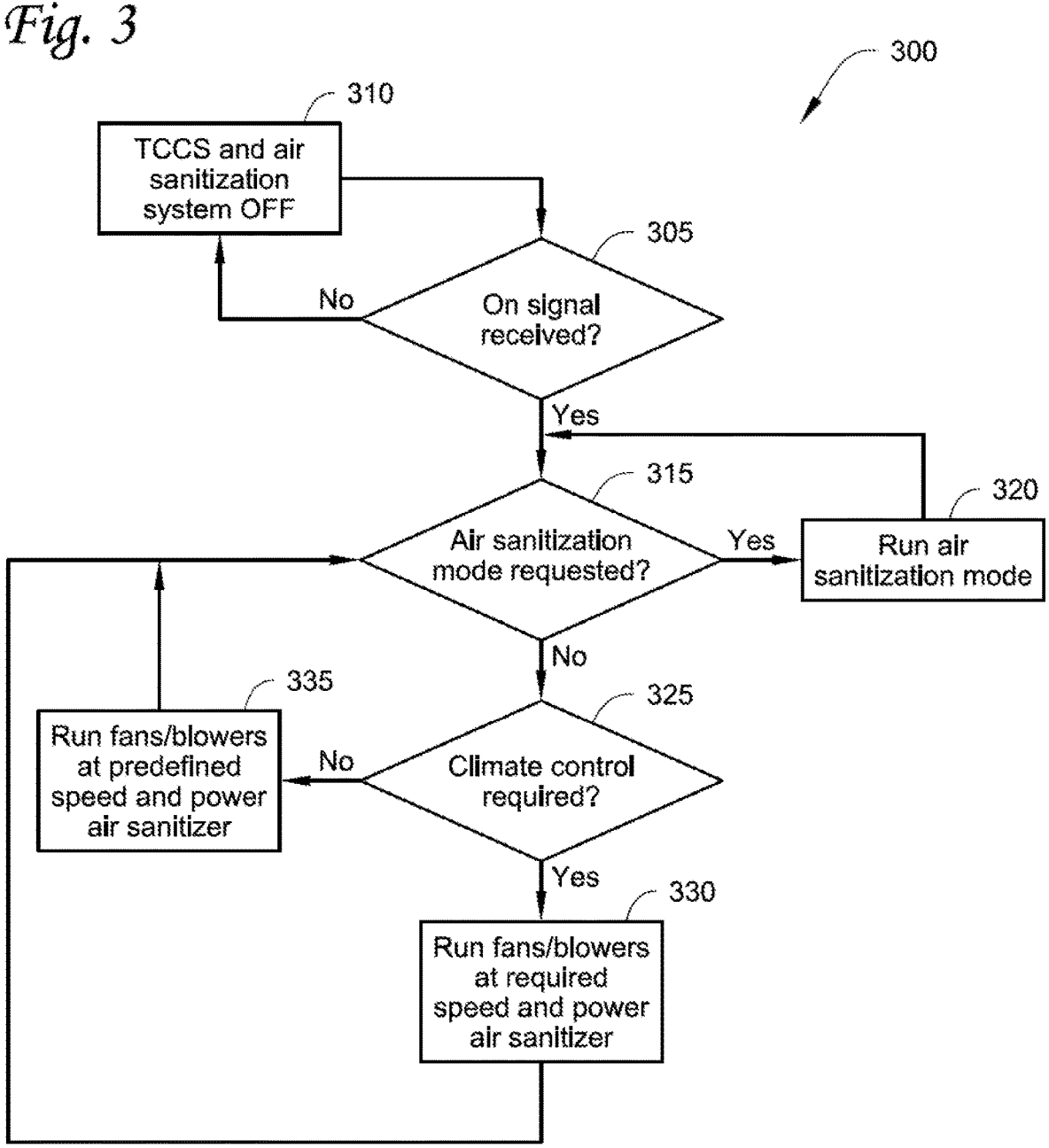
FIG. 3 illustrates a flowchart of a method for controlling operation of the air sanitization system and the transport climate control system shown in FIG. 2, according to one embodiment.

FIG. 3 illustrates a flowchart of a method 300 for controlling operation of the air sanitization system 210 and the transport climate control system 230 shown in FIG. 2, according to one embodiment.

It will be appreciated that the embodiments described herein with respect to the method 300 shown in FIG. 3 are not limited to operating an air sanitization system for a mass-transit vehicle and can be used with other transport units including, for example, the vehicle 10 shown in FIG. 1B, the climate controlled transport unit 105 shown in FIG. 1D, etc. It will also be appreciated that the embodiments described herein with respect to the method 300 shown in FIG. 3 can also be applied in non-transport applications (e.g., residential HVAC applications, commercial HVAC applications, etc.).

The method 300 begins at 305 whereby the controller 255 receives an ON signal. In some embodiments, the ON signal can indicate that the mass-transit vehicle 200 has been turned ON. For example, in some embodiments, the ON signal can be a signal indicating that an ignition switch of the mass-transit vehicle 200 has been turned ON. In some embodiments, the ON signal can indicate that an APU (e.g., the APU 40, 140) has been turned ON. When the controller 255 does not receive the ON signal, the method 300 proceeds to 310. When the controller 255 receives the ON signal, the method 300 proceeds to 315.

At 310, the controller 255 instructs one or more components of the transport climate control system 230 (e.g., one or more of the air movement fans/blowers 245, the compressor, the one or more condenser fans, the one or more valves, etc.) and the air sanitizer 220 to be OFF. For example, in some embodiments, the controller 255 can instruct the air movement fans/blowers 245, the compressor, and the air sanitizer 220 to be OFF. The method 300 then proceeds back to 305.

At 315, the controller 255 determines whether an air sanitization mode has been requested. In some embodiments the air sanitization mode can be manually requested by an operator via, for example, a HMI, a telematics unit, a vehicle controller of the passenger vehicle 200, etc. The instruction can then be sent to the controller 255 via, for example, a controller area network (CAN) message. In some embodiments, the air sanitization mode can be automatically requested. For example, the controller 255 can automatically request the air sanitization mode when the mass-transit vehicle is initially started. In one implementation, the controller 255 can automatically request the air sanitization mode to operate for a set time period (e.g., 10 minutes) once the ON signal is received at 305. Thus, for example, the air in the climate controlled space 202 can be purified prior to the first trip of the day for the mass-transit vehicle 200. In another implementation, the controller 255 can automatically request the air sanitization mode to operate for a set period of time (e.g., 10 minutes) during a larger period of time (e.g., every hour). In yet another example, the controller 255 can monitor the one or more contamination sensors 224. When the indoor air quality (e.g., contamination) level in the climate controlled space 202 exceeds a preset indoor air quality threshold, the controller 255 can automatically request the air sanitization mode to purify/clean the air in the climate controlled space 202. Depending on the indoor air quality level, the controller 255 can also communicate an alarm/maintenance notification to a user via the HMI, the telematics unit, etc.

When the controller 255 determines that the air sanitization mode has been requested, the method 300 proceeds to 320. When the controller 255 determines that the air sanitization mode has not been requested, the method 300 proceeds to 325.

At 320, the controller 255 instructs the air sanitization system 210 and the transport climate control system 230 to operate in the air sanitization mode. In particular, the controller 255 instructs the air sanitizer 220 to turn ON and instructs the air movement fans/blowers 245 to operate at a high speed to increase the speed in which the air sanitization system 210 can purify air within the climate controlled space 202. The controller 255 can also instruct other components of the transport climate control system 230 (e.g., the compressor, the one or more condenser fans, the one or more valves, etc.) to operate as previously instructed, for example, for climate control purposes. If climate control is not required, the controller 255 can instruct the other components of the transport climate control system (e.g., the compressor, the one or more condenser fans, the one or more valves, etc.) to be OFF. In some embodiments, the controller 255 can also reduce the speed of the air movement fans/blowers 245 when desired to conserve energy usage. Accordingly, continuous high speed airflow of purified air can be achieved in the climate controlled space 202.

At 325, the controller 255 determines whether climate control is required for conditioning air in the climate controlled space 202. In some embodiments, the controller 255 can obtain climate control parameter data from the one or more climate control sensors to monitor one or more climate control parameters. The climate control parameters can be used, at least in part, to determine whether conditioned air is required in the climate controlled space 202. The climate control parameters, for example, can include: a return air temperature of air returned from the climate controlled space 202 back to the climate control unit 235; a supply air temperature of air supplied by the CCU 235 into the climate controlled space 122; a humidity within the climate controlled space 202; an ambient temperature outside of the mass-transit vehicle 200; a compressor suction pressure at or near a suction port of the compressor; a compressor discharge pressure at or near a discharge port of the compressor; etc. The one or more climate control parameters can be compared to a threshold value to determine whether climate control within the climate controlled space 202 is required. For example, the return air temperature can be compared to a desired setpoint temperature or an ambient temperature. When the difference between the return air temperature and the desired setpoint temperature (or the ambient temperature) is outside of a boundary range (e.g., 5° Fahrenheit), the controller 255 determines that climate control is required. When the difference between the return air temperature and the desired setpoint temperature is inside of the boundary range, the controller 255 determines that climate control is not required. In another example, the compressor suction pressure or the compressor discharge pressure can be compared to a preset pressure threshold. When the compressor discharge pressure or the compressor suction pressure exceeds the preset pressure threshold, the controller 255 can determine that climate control is required. When the compressor discharge pressure or the compressor suction pressure does not exceed the preset pressure threshold, the controller 255 can determine that climate control is not required.

When the controller 255 determines that climate control is required for conditioning air in the climate controlled space 202, the method 300 proceeds to 330. When the controller 255 determines that climate control is not required for conditioning air in the climate controlled space 202, the method 300 proceeds to 335.

At 330, the controller 255 determines the amount of climate control required for conditioning the climate controlled space 202 and sends appropriate instructions to the components of the transport climate control system 230 (e.g., the air movement fans/blowers 245, the compressor, the one or more condenser fans, the one or more valves, etc.). This includes the controller 255 instructing the air movement devices 245 to be ON and operating at a required non-zero speed (e.g., a low speed, a medium speed, a high speed, etc.). Accordingly, the transport climate control system 230 can provide passenger comfort to passengers in the climate controlled space 202. The controller 255 also instructs the air sanitizer 220 to be ON to purify the conditioned air entering the climate controlled space 202. In some embodiments, the controller 255 can also monitor the one or more contamination sensors 224 and increase the speed of the air movement fans/blowers 245 when the indoor air quality level in the climate controlled space 202 exceeds a preset indoor air quality threshold. Depending on the indoor air quality level, the controller 255 can also communicate an alarm/maintenance notification to a user via the HMI, the telematics unit, etc. In some embodiments, the controller 255 can also reduce the speed of the air movement fans/blowers 245 when desired to conserve energy usage. The method 330 then proceeds back to 315.

At 335, the controller 255 instructs the air sanitizer 220 to turn ON and instructs the air movement fans/blowers 245 to operate at a predefined speed. In some embodiments, the predefined speed can be a low speed of the air movement fans/blowers 245. In some embodiments, the predefined speed can be a speed that is lower than the high speed of the air movement fans/blowers 245. The controller 255 can also instruct one or more other components of the transport climate control system 230 (e.g., one or more of the compressor, the one or more condenser fans, the one or more valves, etc.) to turn OFF. For example, in some embodiments, the controller 255 can instruct the compressor to be OFF. Accordingly, purified air can still be directed to the climate controlled space 202 without requiring conditioning of the purified air. In some embodiments, the controller 255 can also monitor the one or more contamination sensors 224 and increase the speed of the air movement fans/blowers 245 when the indoor air quality level in the climate controlled space 202 exceeds a preset indoor air quality threshold. Depending on the indoor air quality level, the controller 255 can also communicate an alarm/maintenance notification to a user via the HMI, the telematics unit, etc. The method 300 then proceeds back to 315.

In some embodiments, throughout the method 300, the controller 255 can also monitor the one or more contamination sensors 224 for specific problematic species of particles (e.g., halogen particles) and turn OFF the air sanitizer 220 when a certain level of a problematic specie of particles is identified. Also, in some embodiments, throughout the method 300, the controller 255 can monitor the one or more contamination sensors 224 for a total level of contamination within the climate controlled space and turn OFF the air sanitizer 220 when the monitored level of contamination within the climate controlled space exceeds a clean air threshold.

It will be appreciated that in some embodiments, 315 and 320 can be optional such that when the controller 255 receives the ON signal, the method 300 can proceed directly to 325. Also, in some embodiments, when the controller 255 receives the ON signal, the method 300 can proceed directly to 335 to run the air movement fans/blowers 245 and power ON the air sanitizer 220 and then proceed from 335 to 325 to determine whether climate control is required.

An advantage of the method 300 is that the air movement fans/blowers 245 is controlled to be operating whenever the mass-transit vehicle 200 is turned ON in order to provide constant airflow movement within the climate controlled space. Another advantage of the method 300 is that the air sanitizer 220 is always ON (i.e., in use) when there is airflow movement within the climate controlled space. Accordingly, purified air can be provided to the climate controlled space 202 whenever the mass-transit vehicle 200 is ON regardless of whether the transport climate control system 230 is conditioning the airflow. Also, it will be appreciated that in some embodiments, when the air sanitizer 220 is in operation (e.g., at 320, 330 and 335) the controller 255 can selectively turn ON and OFF or reduce power to the individual LED panels of the air sanitizer 220 in order to reduce energy consumption of the air sanitizer 220.

Figure 4:
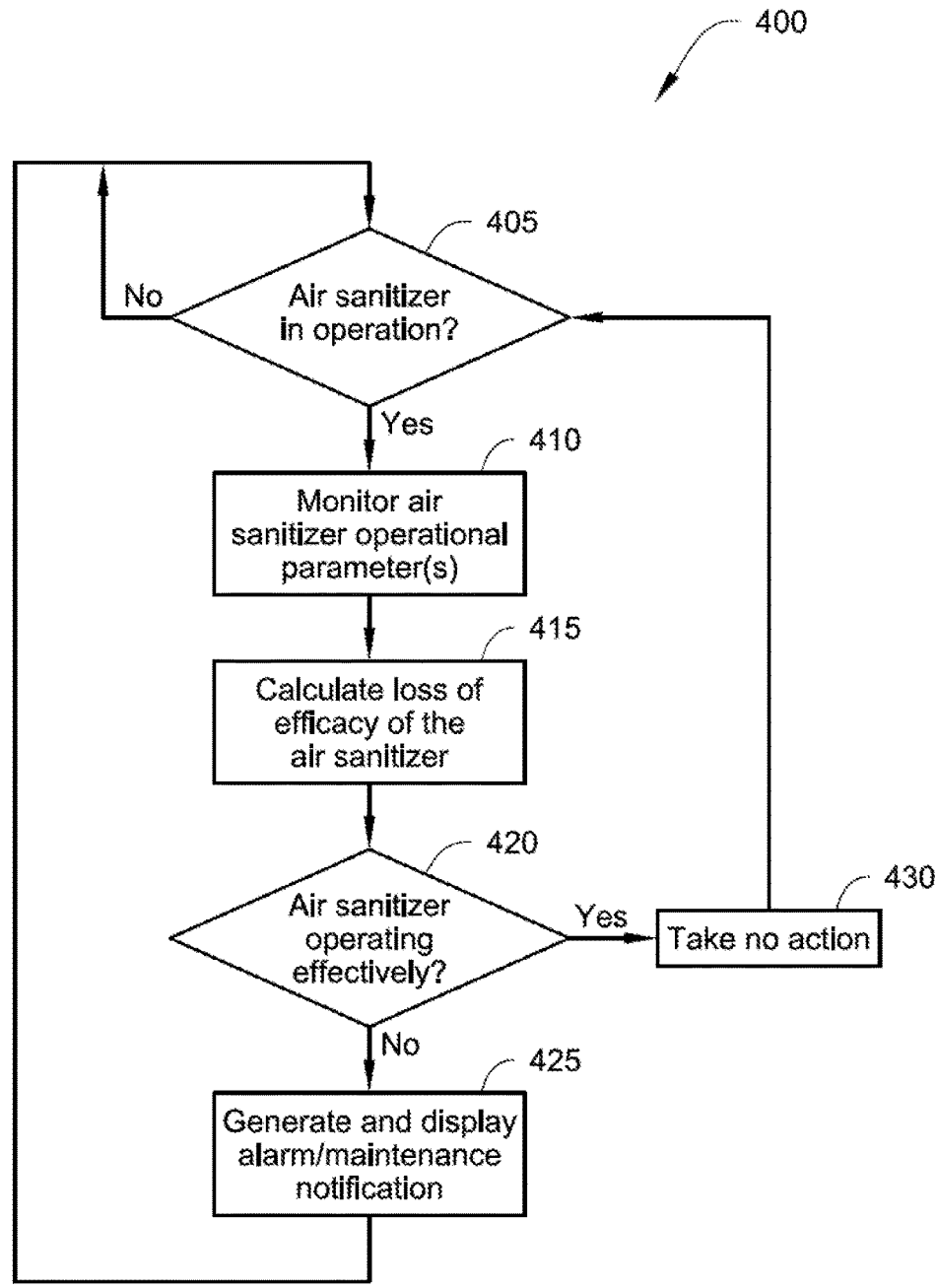
FIG. 4 illustrates a flowchart of a method for tracking effectiveness of the air sanitization system shown in FIG. 2, according to one embodiment.

FIG. 4 illustrates a flowchart of a method 400 for tracking effectiveness of the air sanitization system 210 shown in FIG. 2, according to one embodiment.

It will be appreciated that the embodiments described herein with respect to the method 400 shown in FIG. 4 are not limited to operating an air sanitization system for a mass-transit vehicle and can be used with other transport units including, for example, the vehicle 10 shown in FIG. 1B, the climate controlled transport unit 105 shown in FIG. 1D, etc. It will also be appreciated that the embodiments described herein with respect to the method 400 shown in FIG. 4 can also be applied in non-transport applications (e.g., residential HVAC applications, commercial HVAC applications, etc.).

The method 400 begins at 405 whereby the controller 255 determines whether the air sanitizer 220 has been instructed to operate. When the controller 255 determines that the air sanitizer 220 has been instructed to operate, the method 400 proceeds to 405. When the controller 255 determines that the air sanitizer 220 has been instructed to operate, the method 400 proceeds to 410. When the controller 255 determines that the air sanitizer 220 has not been instructed to operate, the method 400 returns to 405.

At 410, the controller 255 monitors one or more operational parameters of the air sanitizer 220. In some embodiments, the controller 255 can monitor the one or more operational parameters of the air sanitizer 220 by receiving operational parameter data from the one or more operational sensors 222 and/or the one or more contamination sensors 224. The one or more operational parameters can, for example, include: current draw data from the air sanitizer 220 as a whole and/or each of the multiple LED panels and/or each of the multiple LED circuits; power draw data from the air sanitizer 220 as a whole and/or each of the multiple LED panels and/or each of the multiple LED circuits; light intensity data of each of the one or more UV lights; luminance data of each of the multiple LED panels and/or each of the multiple LED circuits; indoor air quality data within the climate controlled space 202; etc. The method 400 then proceeds to 415.

At 415, the controller 255 calculates an amount or percentage in loss of efficacy of the air sanitizer 220 based on the monitored operational data obtained at 410. For example, in some embodiments, the monitored current/power draw data can be compared to an expected current/power draw of the air sanitizer 220. The difference between the monitored current/power draw and the expected current/power draw can be used to calculate a percentage in current/power reduction of the air sanitizer 220 compared to the amount of current/power the air sanitizer 220 is expected to draw. In another example, the monitored current/power draw data can be used to calculate a number of LED circuits that have failed. In yet another example, the controller 255 can calculate the loss of indoor air quality amount or percentage based on the indoor quality data monitored at 410. The method 400 then proceeds to 420.

At 420, the controller 255 determines whether the air sanitization system 210 is operating effectively. In some embodiments, the controller 255 can determine whether the air sanitization system 210 is operating effectively by comparing the amount or percentage in loss of efficacy of the air sanitizer 220 calculated at 415 to a preset efficacy threshold. For example, the calculated percentage in current/power reduction can be compared to a preset current/power reduction threshold. In another example, the number of failed LED circuits calculated at 415 can be compared to a preset failed LED circuit threshold. In yet another example, the loss of indoor air quality amount or percentage can be compared a preset indoor air quality threshold. Also, in another example, the calculated percentage in light intensity or luminance reduction can be compared to a preset light intensity or luminance threshold. When the loss of efficacy of the air sanitizer 220 exceeds the preset efficacy threshold, the controller determines that the air sanitization system 210 is not operating effectively and the method 400 proceeds to 425. When the loss of efficacy of the air sanitizer 220 does not exceed the preset efficacy threshold, the controller determines that the air sanitization system 210 is operating effectively and the method 400 proceeds to 430.

At 425, the controller 255 generates and displays an alarm/maintenance notification to a user via, for example, the HMI, the telematics unit, etc. In some embodiments, the controller 255 can instruct the HMI of the transport climate control system 230 to display an alarm/maintenance notification on a display of the HMI. In some embodiments, the controller 255 can instruct the telematics unit of the transport climate control system 230 to send an alarm/maintenance notification to a user via a wireless communication (e.g., a text message, an email, SMS message, etc.) so that the, for example, alarm/maintenance notification is displayed on the user's mobile device. In some embodiments, the alarm/maintenance notification can include a percentage of the air sanitizer 220 that is in operation. The method 400 then proceeds back to 405.

At 430, the controller 255 takes no further action is taken as the controller 255 determined at 420 that the air sanitization system 210 is operating effectively. The method 400 returns to 405.

Figure 5:
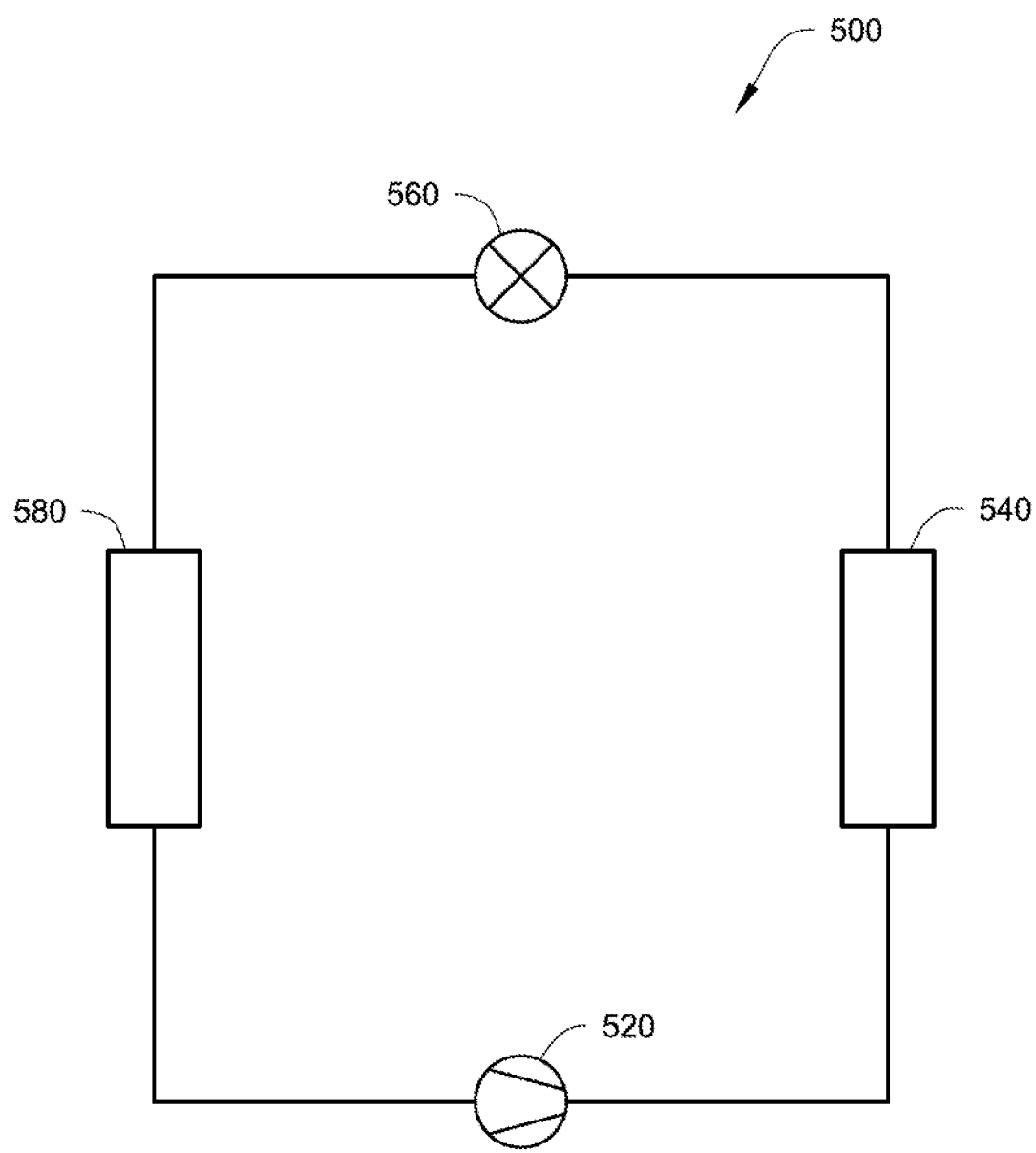
FIG. 5 is a schematic diagram of a refrigeration circuit, which may be implemented in an HVACR system, according to an embodiment.

FIG. 5 is a schematic diagram of a refrigerant circuit 500, according to an embodiment. The refrigerant circuit 500 generally includes a compressor 520, a condenser 540, an expansion device 560, and an evaporator 580. An "expansion device" as described herein may also be referred to as an expander. In an embodiment, the expander may be an expansion valve, expansion plate, expansion vessel, orifice, or the like, or other such types of expansion mechanisms. It should be appreciated that the expander may be any suitable type of expander used in the field for expanding a working fluid to cause the working fluid to decrease in pressure and temperature. In an embodiment, the evaporator 580 can be a microchannel heat exchanger. The refrigerant circuit 500 is an example and can be modified to include additional components. For example, in an embodiment, the refrigerant circuit 500 can include other components such as, but not limited to, an economizer heat exchanger, one or more flow control devices, a receiver tank, a dryer, a suction-liquid heat exchanger, or the like.

The refrigerant circuit 500 can generally be applied in a variety of systems used to control an environmental condition (e.g., temperature, humidity, air quality, or the like) in a space (generally referred to as a conditioned space). Examples of such systems include, but are not limited to, HVACR systems, transport refrigeration systems, or the like. In an embodiment, a HVACR system can be a rooftop unit or a heat pump air-conditioning unit.

The compressor 520, condenser 540, expansion device 560, and evaporator 580 are fluidly connected. In an embodiment, the refrigerant circuit 500 can be configured to be a cooling system (e.g., an air conditioning system) capable of operating in a cooling mode. In an embodiment, the refrigerant circuit 500 can be configured to be a heat pump system that can operate in both a cooling mode and a heating/defrost mode. A centrifugal fan (not shown, described later) can be provided to a heat exchanger such as the condenser 540 and/or the evaporator 580.

It will be appreciated that the centrifugal fans are disclosed in e.g., the U.S. Pat. Nos. 7,591,633; 7,186,080; 7,108,478; 5,570,996; 5,558,499; 3,627,440; 3,307,776; 3,217,976; 2,981,461; 2,951,630; 2,798,658; 2,727,680; 3,221,983; and 1,862,523, the entire disclosure of which are hereby incorporated by reference herein.

The refrigerant circuit 500 can operate according to generally known principles. The refrigerant circuit 500 can be configured to heat and/or cool a liquid process fluid (e.g., a heat transfer fluid or medium (e.g., a liquid such as, but not limited to, water or the like)), in which case the refrigerant circuit 500 may be generally representative of a liquid chiller system. The refrigerant circuit 500 can alternatively be configured to heat and/or cool a gaseous process fluid (e.g., a heat transfer medium or fluid (e.g., a gas such as, but not limited to, air or the like)), in which case the refrigerant circuit 500 may be generally representative of an air conditioner and/or heat pump.

In operation, the compressor 520 compresses a working fluid (e.g., a heat transfer fluid (e.g., refrigerant or the like)) from a relatively lower pressure gas to a relatively higher-pressure gas. The relatively higher-pressure gas is also at a relatively higher temperature, which is discharged from the compressor 520 and flows through the condenser 540. In accordance with generally known principles, the working fluid flows through the condenser 540 and rejects heat to the process fluid (e.g., water, air, etc.), thereby cooling the working fluid. The cooled working fluid, which is now in a liquid form, flows to the expansion device 560. The expansion device 560 reduces the pressure of the working fluid. As a result, a portion of the working fluid is converted to a gaseous form. The working fluid, which is now in a mixed liquid and gaseous form flows to the evaporator 580. The working fluid flows through the evaporator 580 and absorbs heat from the process fluid (e.g., a heat transfer medium (e.g., water, air, etc.)), heating the working fluid, and converting it to a gaseous form. The gaseous working fluid then returns to the compressor 120. The above-described process continues while the heat transfer circuit is operating, for example, in a cooling mode (e.g., while the compressor 520 is enabled).

Figure 6:
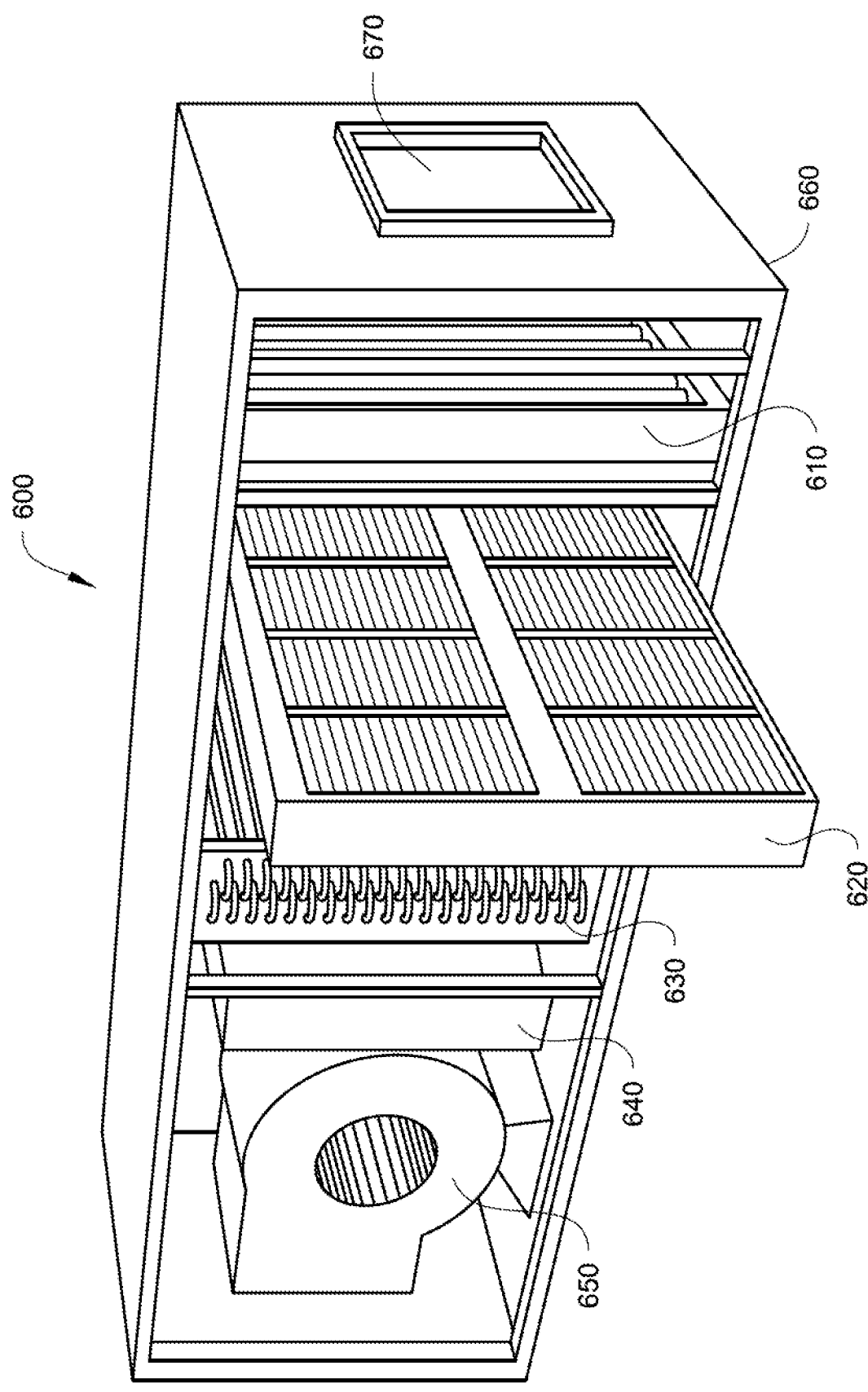
FIG. 6 is a perspective view, partially cutaway, illustrating an air handling unit of an HVACR system having a centrifugal fan, according to an embodiment.

FIG. 6 is a perspective view, partially cutaway, illustrating an air handling unit (air handler) 600 of an HVACR system having a centrifugal fan 650, according to an embodiment.

The unit 600 includes an enclosure 660. In one embodiment, the enclosure 660 can be a generally rectangular cabinet having a first end wall defining an air inlet opening 670 (to allow air to flow into an internal space of the enclosure 660) and a second end wall defining an air outlet opening (not shown, to allow air to flow out of the enclosure 660 via an air outlet (that overlaps with the air outlet opening) of the centrifugal fan 650. In FIG. 6, a side wall of the enclosure 660 is cutaway and the internal space of the enclosure 660 is shown.

The unit 600 also includes a primary filter 610 and a secondary filter 620. In one embodiment, the primary filter 610 and the secondary filter 620 can be one filter. It will be appreciated that the primary filter 610 and/or the secondary filter 620 can be a porous device configured to remove impurities or solid particles from air flow passed through the device.

In one embodiment, outer surface(s) (e.g., the entire surface facing the airflow and/or the entire surface opposite to the surface facing the airflow) of the secondary filter 620 (and/or the primary filter 610) can be covered (or coated or sintered) with e.g., a photocatalyst layer. A light source (not shown) can be added in the enclosure 660 to emit light on the photocatalyst layer disposed on the outer surface(s) of the filter where the air passes through. This embodiment provides a solution to achieve photocatalytic oxidation and/or ultraviolet germicidal irradiation on surfaces of the filter (s). In this embodiment, more space is needed (e.g., for disposing the light source) in the enclosure 660 (and thus a length of the enclosure may need to be increased, or the space of other components within the enclosure 660 may be occupied by the light source), air pressure drop may occur (e.g., due to the added resistance to the air because of the added photocatalyst layer to the filter) on the outer surface(s) of the filter, and/or a sealed installation may be needed (e.g., for the light source to prevent e.g., UV light such as UVC light from being leaked out from the enclosure 660). In this embodiment, the efficiency and efficacy of one-time filtration and/or sterilization of air can be optimal because e.g., the outer surface(s) of the filter may cover the entire airflow passing through the filter.

The unit 600 further includes a component (e.g., a coil) 630. In one embodiment, the component 630 can be an air conditioning evaporator coil disposed in the flow path of air passing from the air inlet opening 670 to the air outlet opening of the enclosure 660 (which is also the air outlet of the fan 650). It will be appreciated that the component 630 can be different types in that the working fluid can be e.g., refrigerant, water, or the like. For example, when the working fluid is refrigerant, the component 630 can be an evaporator coil for cooling, and/or can be a condenser coil for heating. For example, when the working fluid is water, the component 630 can be tube(s) for chilled water to go through for cooling, and can be tube(s) for hot water to go through for heating.

The unit 600 also includes a humidifier 640 configured to add moisture to the air to prevent dryness that can cause irritation in many parts of the human body or to increase humidity in the air.

Also the unit 600 includes a fan (or blower) 650. In one embodiment, the fan 650 can be a centrifugal fan having electric drive motor (not shown) to drive the fan 650 (e.g., to drive a shaft of the fan 650, to rotate the impeller of the fan 650). It will be appreciated that a centrifugal fan is a mechanical device for moving air or other gases toward the outlet of the fan in a direction at an angle (e.g., perpendicular) to the incoming air from the inlet of the fan. A centrifugal fan often contains a ducted housing to direct outgoing air in a specific direction or across a heat sink. The centrifugal fan can increase the speed and volume of an air stream with rotating impellers.

Returning to FIG. 2, in some embodiments, the mass-transit vehicle 200 can include the air sanitization system 210 but not include the transport climate control system 230. In these embodiments, the air sanitization system 210 can have its own unit that includes its own air movement fan/blower(s) to provide air purification within a space of the mass-transit vehicle 200. Also, in these embodiments, the evaporator coil 240 would not be provided and the controller 255 would be a controller configured to control the air sanitization system 210 but not a climate control system. In these embodiments, the method 300 can be adjusted by removing 325 and 330. Accordingly, when the air sanitization mode is not requested 315, the method will proceed directly to 335.

Aspects:

It is noted that any of aspects 1-42 can be combined.

Aspect 1. A method for purifying air within a climate controlled space, the method comprising:
  a controller determining whether climate control is required for conditioning air within the climate controlled space;
  upon determining that climate control is required, the controller:
    determining an amount of climate control required for conditioning air within the climate controlled space,
    instructing a compressor of a climate control system to operate to meet the amount of climate control required,
    instructing an air movement fan/blower of the climate control system to operate to meet the amount of climate control required, and
    instructing operation of an air sanitizer of an air sanitization system; and upon determining that climate control is not required, the controller:
    instructing an air movement fan/blower of the climate control system to operate at a predefined speed, and
    instructing operation of an air sanitizer of the air sanitization system.

Aspect 2. The method of aspect 1, further comprising:
  the controller determining whether an ON signal is received;
  the controller determining whether climate control is required for conditioning air within the climate controlled space when the ON signal is received; and
  the controller instructing the compressor, the air movement fan/blower, and the air sanitizer to be OFF when the ON signal is not received.

Aspect 3. The method of any one of aspects 1 and 2, further comprising:
  the controller determining whether an air sanitization mode is requested; and
  upon the controller determining that the air sanitization mode is requested, the controller:
    instructing the air movement fan/blower of the climate control system to operate at a high speed; and
    instructing operation of the air sanitizer of the air sanitization system.

Aspect 4. The method of any one of aspects 1-3, wherein upon determining that climate control is not required, the controller further instructing the compressor of the climate control system to be OFF.

Aspect 5. A system for purifying air within a climate controlled space, the system comprising:
  an air sanitization system, the air sanitization system including an air sanitizer configured to purify air passing through the air sanitization system;
  a climate control system, the climate control system including:
    a compressor configured to compress a working fluid;
    an evaporator coil configured to condition air passing over the evaporator coil; and
    an air movement fan/blower configured to direct conditioned air from the evaporator coil to the climate controlled space;
  wherein the air sanitizer is positioned such that a majority of air passing over the evaporator coil is purified by the air sanitizer.

Aspect 6. The system of aspect 5, wherein the air sanitization system further includes a filter positioned upstream of the air sanitizer, wherein the filter is configured to trap contaminants from air passing there through.

Aspect 7. The system of any one of aspects 5 and 6, further comprising a controller configured to control operation of the air sanitization system and the climate control system.

Aspect 8. The system of aspect 7, wherein the controller is configured to:
  determine whether climate control is required for conditioning air within the climate controlled space;
  upon determining that climate control is required, the controller is configured to:
    determine an amount of climate control required for conditioning air within the climate controlled space,
    instruct the compressor of the climate control system to operate to meet the amount of climate control required,
    instruct the air movement fan/blower of the climate control system to operate to meet the amount of climate control required, and
    instruct operation of the air sanitizer of an air sanitization system; and upon determining that climate control is not required, the controller:
    instruct the air movement fan/blower of the climate control system to operate at a predetermined speed, and
    instruct operation of an air sanitizer of the air sanitization system.

Aspect 9. The system of any one of aspects 7 and 8, wherein the controller is configured to:
monitor an operational parameter of the air sanitizer;
determine that the air sanitizer is not operating effectively based on the operational parameter; and
generate and display an alarm/maintenance notification to a user upon the controller determining that the air sanitizer is not operating effectively.

Aspect 10. The system of aspect 5, wherein the air sanitizer is a photo catalytic oxidation (PCO) air purifier.

Aspect 11. The system of aspect 10, wherein the air sanitizer is a graphene based PCO air purifier configured to use a graphene enhanced titanium oxide catalyst to generate hydroxyls.

Aspect 12. A method for tracking effectiveness of an air sanitization system that includes an air sanitizer, the method comprising:
a controller monitoring an operational parameter of the air sanitizer;
the controller determining that the air sanitizer is not operating effectively based on the operational parameter; and
generating and displaying an alarm/maintenance notification to a user upon the controller determining that the air sanitizer is not operating effectively.

Aspect 13. The method of aspect 12, further comprising the controller calculating a loss of efficacy of the air sanitizer based on the monitored operational parameter,
wherein the controller determines that the air sanitizer is not operating effectively based on the calculated loss of efficacy of the air sanitizer.

Aspect 14. The method of any one of aspects 12 and 13, wherein the operational parameter is at least one of a current draw of a light emitting diode (LED) circuit of the air sanitizer, a power draw of the LED circuit of the air sanitizer, a light intensity of an ultraviolet (UV) light of the air sanitizer, a luminance of the LED circuit of the air sanitizer, and an indoor air quality of the climate controlled space.

Aspect 15. A method for purifying air within a space, the method comprising:
a controller determining whether an ON signal is received;
upon determining that the ON signal is received, the controller instructing:
an air sanitizer of an air sanitization system to turn ON to purify an airflow passing through the air sanitization system, and
an air movement fan/blower to operate in order to direct the airflow into the space, and
and
upon determining that the ON signal is not received, the controller instructing the air movement fan/blower and the air sanitizer to be OFF.

Aspect 16. The method of aspect 15, wherein, upon determining that the ON signal is received, the controller determining that climate control is not required for conditioning air within the space, and
upon determining that climate control is not required, the controller:
instructing the air sanitizer to be ON,
instructing the air movement fan/blower to operate at a predefined speed, and
instructing a compressor of a climate control system to be OFF.

Aspect 17. The method of aspect 16, wherein the air movement fan/blower has a low speed and a high speed, and wherein the predefined speed is the low speed.

Aspect 18. The method of any one of aspects 15-17, wherein, upon determining that the ON signal is received, the controller determining that climate control is required for conditioning air within the space, and
upon determining that climate control is required, the controller:
determining an amount of climate control required for conditioning air within the space,
instructing a compressor of a climate control system to operate to meet the amount of climate control required, and
instructing the air movement fan/blower to operate to meet the amount of climate control required.

Aspect 19. The method of any one of aspects 15-18, wherein the controller determining whether the ON signal is received includes the controller determining whether a vehicle having or towing the space is turned ON.

Aspect 20. The method of aspect 19, wherein the ON signal indicates that an ignition switch of the vehicle has been turned ON.

Aspect 21. The method of any one of aspects 15-20, further comprising:
upon determining that the ON signal is received, the controller determining whether an air sanitization mode is requested; and
upon the controller determining that the air sanitization mode is requested, the controller:
instructing the air movement fan/blower to operate at a high speed; and
instructing operation of the air sanitizer of the air sanitization system.

Aspect 22. A system for purifying air within a space, the system comprising:
an air sanitization system, the air sanitization system including an air sanitizer configured to purify an airflow passing through the air sanitization system;
an air movement fan/blower configured to direct the airflow into the space; and
a controller configured to:
determine whether an ON signal is received,
upon determining that the ON signal is received, instruct:
the air sanitizer to turn ON to purify the airflow passing through the air sanitization system, and
the air movement fan/blower to operate in order to direct the airflow into the space, and
and
upon determining that the ON signal is not received, instruct the air movement fan/blower and the air sanitizer to be OFF.

Aspect 23. The system of aspect 22, wherein, upon the controller determining that the ON signal is received, the controller is configured to determine whether climate control is not required for conditioning air within the space, and
upon the controller determining that climate control is not required, the controller is configured to:
instruct the air sanitizer to be ON,
instruct the air movement fan/blower to operate at a predefined speed, and
instruct a compressor of a climate control system to be OFF.

Aspect 24. The system of aspect 23, wherein the air movement fan/blower has a low speed and a high speed, and wherein the predefined speed is the low speed.

Aspect 25. The system of any one of aspects 22-24, wherein, upon the controller determining that the ON signal is received, the controller is configured to determine whether climate control is required for conditioning air within a climate controlled space, and upon the controller determining that climate control is required, the controller is configured to:
determine an amount of climate control required for conditioning air within the space,
instruct a compressor of a climate control system to operate to meet the amount of climate control required, and
instruct the air movement fan/blower of the climate control system to operate to meet the amount of climate control required.

Aspect 26. The system of any one of aspects 22-25, wherein the controller is configured to determine whether the ON signal is received includes the controller being configured to determine whether a vehicle having or towing the space is turned ON.

Aspect 27. The system of aspect 26, wherein the ON signal indicates that an ignition switch of the vehicle has been turned ON.

Aspect 28. The system of any one of aspects 22-27, further wherein, upon determining that the ON signal is received, the controller is configured to determine whether an air sanitization mode is requested; and upon the controller determining that the air sanitization mode is requested, the controller is configured to:
instruct the air movement fan/blower to operate at a high speed; and
instruct operation of the air sanitizer of the air sanitization system.

Aspect 29. A method for purifying air within a climate controlled space, the method comprising:
a controller determining whether an ON signal is received;
upon determining that the ON signal is received, the controller instructing:
an air sanitizer of an air sanitization system to turn ON to purify an airflow passing through the air sanitization system, and
an air movement fan/blower of a climate control system to operate in order to direct the airflow into the climate controlled space, and
and
upon determining that the ON signal is not received, the controller instructing the air movement fan/blower and the air sanitizer to be OFF.

Aspect 30. The method of aspect 29, wherein, upon determining that the ON signal is received, the controller determining that climate control is not required for conditioning air within the climate controlled space, and upon determining that climate control is not required, the controller:
instructing the air sanitizer to be ON,
instructing the air movement fan/blower to operate at a predefined speed, and
instructing a compressor of the climate control system to be OFF.

Aspect 31. The method of aspect 30, wherein the air movement fan/blower has a low speed and a high speed, and wherein the predefined speed is the low speed.

Aspect 32. The method of any one of aspects 29-31, wherein, upon determining that the ON signal is received, the controller determining that climate control is required for conditioning air within the climate controlled space, and upon determining that climate control is required, the controller:
determining an amount of climate control required for conditioning air within the climate controlled space,
instructing a compressor of a climate control system to operate to meet the amount of climate control required, and
instructing the air movement fan/blower to operate to meet the amount of climate control required.

Aspect 33. The method of any one of aspects 29-32, wherein the controller determining whether the ON signal is received includes the controller determining whether a vehicle having the climate controlled space is turned ON.

Aspect 34. The method of aspect 33, wherein the ON signal indicates that an ignition switch of the vehicle has been turned ON.

Aspect 35. The method of any one of aspects 29-34, further comprising:
upon determining that the ON signal is received, the controller determining whether an air sanitization mode is requested; and
upon the controller determining that the air sanitization mode is requested, the controller:
instructing the air movement fan/blower of the climate control system to operate at a high speed; and
instructing operation of the air sanitizer of the air sanitization system.

Aspect 36. A system for purifying air within a climate controlled space, the system comprising:
an air sanitization system, the air sanitization system including an air sanitizer configured to purify an airflow passing through the air sanitization system;
a climate control system, the climate control system including an air movement fan/blower configured to direct the airflow into the climate controlled space; and
a controller configured to:
determine whether an ON signal is received,
upon determining that the ON signal is received, instruct:
the air sanitizer to turn ON to purify the airflow passing through the air sanitization system, and
the air movement fan/blower to operate in order to direct the airflow into the climate controlled space, and
and
upon determining that the ON signal is not received, instruct the air movement fan/blower and the air sanitizer to be OFF.

Aspect 37. The system of aspect 36, wherein, upon the controller determining that the ON signal is received, the controller is configured to determine whether climate control is not required for conditioning air within the climate controlled space, and upon the controller determining that climate control is not required, the controller is configured to:
instruct the air sanitizer to be ON,
instruct the air movement fan/blower to operate at a predefined speed, and
instruct a compressor of the climate control system to be OFF.

Aspect 38. The system of aspect 37, wherein the air movement fan/blower has a low speed and a high speed, and wherein the predefined speed is the low speed.

Aspect 39. The system of any one of aspects 36-38, wherein, upon the controller determining that the ON signal is received, the controller is configured to determine whether climate control is required for conditioning air within the climate controlled space, and upon the controller determining that climate control is required, the controller is configured to:
determine an amount of climate control required for conditioning air within the climate controlled space,
instruct a compressor of a climate control system to operate to meet the amount of climate control required, and
instruct the air movement fan/blower of the climate control system to operate to meet the amount of climate control required.

Aspect 40. The system of any one of aspects 36-39, wherein the controller is configured to determine whether the ON signal is received includes the controller being configured to determine whether a vehicle having the climate controlled space is turned ON.

Aspect 41. The system of aspect 40, wherein the ON signal indicates that an ignition switch of the vehicle has been turned ON.

Aspect 42. The system of any one of aspects 36-41, further wherein, upon determining that the ON signal is received, the controller is configured to determine whether an air sanitization mode is requested; and
upon the controller determining that the air sanitization mode is requested, the controller is configured to:
instruct the air movement fan/blower of the climate control system to operate at a high speed; and
instruct operation of the air sanitizer of the air sanitization system.

The terminology used in this Specification is intended to describe particular embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This Specification and the embodiments described are exemplary only, with the true scope and spirit of the disclosure being indicated by the claims that follow.

What is claimed is:

1. A method for purifying air within a climate controlled space, the method comprising:
a controller determining whether an ON signal is received;
the controller determining whether climate control is required for conditioning air within the climate controlled space;
upon determining that the ON signal is received and that the climate control is not required for conditioning the air within the climate controlled space, the controller instructing:
an air sanitizer of an air sanitization system to turn ON to purify an airflow passing through the air sanitization system, and
an air movement fan/blower of a climate control system to operate in order to direct the airflow into the climate controlled space, and
one of more components of the climate control system to be OFF, such that the airflow is directed into the climate controlled space without conditioning by the climate control system; and
upon determining that the ON signal is not received, the controller instructing the air movement fan/blower and the air sanitizer to be OFF.

2. The method of claim 1, wherein, upon determining that the ON signal is received that the climate control is not required for conditioning the air within the climate controlled space, the controller:
instructing the air movement fan/blower to operate at a predefined speed,
wherein instructing of the one of more components of the climate control system to be OFF includes instructing a compressor of the climate control system to be OFF.

3. The method of claim 2, wherein the air movement fan/blower has a low speed and a high speed, and wherein the predefined speed is the low speed.

4. The method of claim 1, wherein, upon determining that the ON signal is received and that determining that climate control is required for conditioning the air within the climate controlled space, the controller:
determining an amount of climate control required for conditioning air within the climate controlled space,
instructing a compressor of the climate control system to operate to meet the amount of climate control required, and
instructing the air movement fan/blower to operate to meet the amount of climate control required.

5. The method of claim 1, wherein the controller determining whether the ON signal is received includes the controller determining whether a vehicle having the climate controlled space is turned ON.

6. The method of claim 5, wherein the ON signal indicates that an ignition switch of the vehicle has been turned ON.

7. The method of claim 1, further comprising:
upon determining that the ON signal is received, the controller determining whether an air sanitization mode is requested; and
upon the controller determining that the air sanitization mode is requested, the controller:
instructing the air movement fan/blower of the climate control system to operate at a high speed; and
instructing the air sanitizer to be ON to purify the airflow passing through the air sanitization system.

8. The method of claim 1,
wherein, upon determining that the ON signal is received that the climate control is not required for conditioning the air within the climate controlled space, the controller instructing the air movement fan/blower to operate at a predefined speed,
wherein the method further comprises:
upon determining that the ON signal is received, the controller determining whether an air sanitization mode is requested; and
upon the controller determining that the air sanitization mode is requested, the controller:
instructing the air movement fan/blower of the climate control system to operate at a high speed, high speed being a speed higher than the predefined speed; and
instructing the air sanitizer to be ON to purify the airflow passing through the air sanitization system.

9. The method of claim 1, wherein the air sanitizer is configured to purify the airflow by attacking volatile organic compounds in the airflow.

10. A system for purifying air within a climate controlled space, the system comprising:
- an air sanitization system, the air sanitization system including an air sanitizer configured to purify an airflow passing through the air sanitization system;
- a climate control system, the climate control system including an air movement fan/blower configured to direct the airflow into the climate controlled space; and
- a controller configured to:
  - determine whether an ON signal is received, and
  - determine whether climate control is required for conditioning air within the climate controlled space,
  - upon determining that the ON signal is received and that the climate control is not required for conditioning the air within the climate controlled space, instruct:
    - the air sanitizer to turn ON to purify the airflow passing through the air sanitization system, and
    - the air movement fan/blower to operate in order to direct the airflow into the climate controlled space, and
    - one of more components of the climate control system to be OFF, such that the airflow is directed into the climate controlled space without conditioning by the climate control system; and
  - upon determining that the ON signal is not received, instruct the air movement fan/blower and the air sanitizer to be OFF.

11. The system of claim 10, wherein, upon the controller determining that the ON signal is received that the climate control is not required for conditioning the air within the climate controlled space, the controller is configured to:
- instruct the air movement fan/blower to operate at a predefined speed,
- wherein the controller being configured to instruct one or more components of the climate control system to be OFF includes the controller instructing a compressor of the climate control system to be OFF.

12. The system of claim 11, wherein the air movement fan/blower has a low speed and a high speed, and wherein the predefined speed is the low speed.

13. The system of any one of claim 10, wherein, upon the controller determining that the ON signal is received that the climate control is required for conditioning the air within the climate controlled space, the controller is configured to:
- determine an amount of climate control required for conditioning the air within the climate controlled space,
- instruct a compressor of the climate control system to operate to meet the amount of climate control required, and
- instruct the air movement fan/blower of the climate control system to operate to meet the amount of climate control required.

14. The system of claim 10, wherein the controller is configured to determine whether the ON signal is received includes the controller being configured to determine whether a vehicle having the climate controlled space is turned ON.

15. The system of claim 14, wherein the ON signal indicates that an ignition switch of the vehicle has been turned ON.

16. The system of claim 10, wherein, upon determining that the ON signal is received, the controller is configured to determine whether an air sanitization mode is requested; and
- upon the controller determining that the air sanitization mode is requested, the controller is configured to:
  - instruct the air movement fan/blower of the climate control system to operate at a high speed; and
  - instruct the air sanitizer to be ON to purify an airflow passing through the air sanitization system.

17. The system of claim 10,
- wherein, upon determining that the ON signal is received and that the climate control is not required for conditioning the air within the climate controlled space, the controller is configured to instruct the air movement fan/blower to operate at a predefined speed, and
- wherein, upon determining that the ON signal is received, the controller is configured to determine whether an air sanitization mode is requested; and
- upon the controller determining that the air sanitization mode is requested, the controller is configured to:
  - instruct the air movement fan/blower of the climate control system to operate at a high speed, the high speed being a speed higher than the predefined speed; and
  - instruct the air sanitizer to turn ON to purify an airflow passing through the air sanitization system.

18. The system of claim 10, wherein the air sanitizer is configured to purify the airflow by attacking volatile organic compounds in the airflow.

* * * * *